United States Patent
Kunos et al.

(10) Patent No.: US 10,077,446 B2
(45) Date of Patent: Sep. 18, 2018

(54) GLUCAN-ENCAPSULATED SIRNA FOR TREATING TYPE 2 DIABETES MELLITUS

(71) Applicants: The United States of America, as represented by THE SECRETARY, DEPT. OF HEALTH AND HUMAN SERVICES, Washington, DC (US); UNIVERSITY OF MASSACHUSETTS, Boston, MA (US)

(72) Inventors: George Kunos, Bethesda, MD (US); Tony Jourdan, Rockville, MD (US); Michael Paul Czech, Worcester, MA (US); Myriam Aouadi, Worcester, MA (US)

(73) Assignees: The United States of America, as represented by the Secretary, Dept. of Health and Human Services, Washington, DC (US); University of Massachusetts, Boston, MA (US)

( * ) Notice: Subject to any disclaimer, the term of this patent is extended or adjusted under 35 U.S.C. 154(b) by 0 days.

(21) Appl. No.: 14/900,951

(22) PCT Filed: Jun. 24, 2014

(86) PCT No.: PCT/US2014/043924
§ 371 (c)(1),
(2) Date: Dec. 22, 2015

(87) PCT Pub. No.: WO2014/210041
PCT Pub. Date: Dec. 31, 2014

(65) Prior Publication Data
US 2016/0138028 A1    May 19, 2016

Related U.S. Application Data

(60) Provisional application No. 61/839,239, filed on Jun. 25, 2013.

(51) Int. Cl.
*C12N 15/11* (2006.01)
*C12N 15/113* (2010.01)
*A61K 31/713* (2006.01)

(52) U.S. Cl.
CPC ........ *C12N 15/1138* (2013.01); *A61K 31/713* (2013.01); *C12N 2310/14* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

| 5,939,429 | A  | 8/1999 | Kunos et al. |
| 2009/0226528 | A1 | 9/2009 | Czech et al. |

FOREIGN PATENT DOCUMENTS

| WO | WO 2004/096763 | 11/2004 |
| WO | WO 2006/108581 | 10/2006 |
| WO | WO 2008/122618 | 10/2008 |
| WO | WO 2009/043353 | 4/2009 |
| WO | WO 2012-120026 A1 | 9/2012 |

OTHER PUBLICATIONS

Laezza et al, The anandamide analog, Met-F-AEA, controls human breast cancer cell migration via the RHOA/RHO kinase signaling pathway, 2008, Endocrine-Related Cancer, 15: 965-974.*
WO 2011/119887, Khvorova et al, Sep. 2011, partial document of pp. 1-122 and Table 23 (130 pages total).*
Nam, D.H. et al., "Blockade of cannabinoid receptor 1 improves insulin resistance, lipid metabolism, and diabetic nephropathy in db/db mice" Endocrinology, Jan. 10, 2012, vol. 153, No. 3, pp. 1389-1396.
De Miguel-Yanes, Jose M. et al., "Variants at the endocannabinoid receptor CB1 gene (CNR1) and insulin sensitivity, type 2 diabetes, and coronary heart disease" Obesity, Jun. 2, 2011, vol. 19, No. 10, pp. 2031-2037.
International Search Report and Written Opinion prepared by the Korean Intellectual Property Office dated Oct. 8, 2014, for International Application No. PCT/US2014/043924.
Extended Search Report for European Patent Application No. 14818342.9, dated Jan. 20, 2017 10 pages.
Official Action for European Patent Application No. 14818342.9, dated Feb. 6, 2018 7 pages.

* cited by examiner

*Primary Examiner* — Ekaterina Poliakova-Georga
(74) *Attorney, Agent, or Firm* — Sheridan Ross P.C.

(57) ABSTRACT

Compositions comprising glucan-encapsulated siRNA directed against a region of the gene encoding the human CB1 receptor for use in the treatment of type 2 diabetes mellitus in a human subject. Additionally, methods for treating type 2 diabetes mellitus in a subject, comprising administering to the subject a composition comprising glucan-encapsulated siRNA directed against the CB1 receptor.

15 Claims, 13 Drawing Sheets
Specification includes a Sequence Listing.

GLUCAN-ENCAPSULATED SIRNA FOR TREATING TYPE 2 DIABETES MELLITUS

RELATED APPLICATIONS

This application is a national stage application under 35 U.S.C. 371 and claims the benefit of PCT Application No. PCT/US2014/043924 having an international filing date of 24 Jun. 2014, which designated the United States, which PCT application claimed the benefit of priority to U.S. Provisional Patent Application No. 61/839,239, filed Jun. 25, 2013, which is incorporated herein by reference.

REFERENCE TO A SEQUENCE LISTING

This application contains a Sequence Listing submitted electronically as a text file. The text file, named "6137NIAAA-2-PCT_sequence_listing_ST25.txt," has a size in bytes of 29 KB, and was created on Jun. 24, 2014. The information contained in the text file is incorporated herein by reference in its entirety pursuant to 37 CFR § 1.52(e)(5).

BACKGROUND

Type 2 diabetes mellitus (T2DM) progresses from a state of insulin resistance with euglycemia and hyperinsulinemia to β-cell failure resulting in impaired insulin secretion and fasting hyperglycemia. The pathogenic role of inflammation in both stages of T2DM is increasingly recognized. Adipose tissue inflammation contributes to insulin resistance via proinflammatory cytokines such as TNFα and IL-6, and infiltration of proinflammatory cells into pancreatic islets of diabetic patients and animals may contribute to β-cell failure. Furthermore, the Nlrp3 (NOD-like receptor family, pyrin domain containing 3) inflammasome, a protein complex involved in the proteolytic activation of caspase-1 and interleukin-1β (IL-1β) secretion, has been implicated in the pathogenesis of diabetogenic insulitis (i.e. inflammation of pancreatic islets).

Endocannabinoids, the lipid ligands of G protein-coupled CB1 and CB2 receptors, produce a broad range of biological effects (reviewed in Pacher, P., et. al., Pharmacol Rev 58, 389-462 (2006)). CB1R (CB1 receptor) activation promotes food intake, increases lipogenesis in adipose tissue and liver, and induces insulin resistance and dyslipidemia, suggesting that an overactive endocannabinoid/CB1R system contributes to the development of visceral obesity and its complications. Accordingly, chronic $CB_1R$/CB1R blockade reduced body weight and improved obesity-related insulin resistance, dyslipidemia and fatty liver both in rodent models of obesity and in overweight people with the metabolic syndrome. CB1R blockade also improved glycemic control as a monotherapy in drug-naive patients with T2DM. However, the therapeutic development of CB1R antagonist/inverse agonists has been halted due to adverse psychiatric effects.

SUMMARY OF THE EMBODIMENTS

Sequence-specific siRNA binds to a target nucleic acid sequence and regulates expression of a gene. Disclosed herein are compositions including glucan-encapsulated siRNA targeting the human CB1R gene (CNR1) and methods of using such compositions to knock down the expression of the receptors selectively on macrophages. Methods are provided wherein targeting specific regions of the CB1R gene by siRNAs for knockdown of gene expression is effective in the treatment of type 2 diabetes mellitus (T2DM). Drug discovery strategies are likewise encompassed within the invention.

Thus, in one aspect, the invention provides a method for treating type 2 diabetes mellitus in a subject, comprising administering to the subject a composition comprising glucan-encapsulated siRNA, wherein the siRNA is directed against CNR1 (the gene encoding the human CB1 receptor), and wherein the glucan encapsulation results in uptake of the siRNA by macrophages. The macrophages can be phagocytic macrophages.

In one embodiment of a method according to the invention, the uptake of the siRNA by macrophages results in selective knockdown of CB1 receptors in the macrophages.

In another embodiment of a method according to the invention, the siRNA is directed against a region in the human CB1R gene (CNR1) substantially corresponding to the rat $CB_1R$ gene (cnr1) region targeted by an siRNA that comprises: i) a sense sequence GCAUCAAGAGCAC-CGUUAAUU (SEQ ID NO:9) and an antisense sequence UUAACGGUGCUCUUGAUGCUU (SEQ ID NO:10). The identification of these sense and antisense sequences was based on in vitro and in vivo studies done in the rat model. The optimum human siRNA sequences (and region of CB1R target gene, CNR1) may vary slightly, although the rat $CB_1R$ and human CB1R gene sequences are very similar. Thereafter, human CNR1 target sequences for siRNA were identified by testing the ability of such siRNAS to knock down CNR1 expression in a human macrophage cell line that expresses CB1R, as described in detail below.

In still another embodiment of a method according to the invention, the siRNA is directed against a region of CNR1. In another embodiment, the region is that region of the gene for which knockdown of the receptors upon uptake of siRNA by a human macrophage cell line is most effective. In another embodiment, the region is comprised within the open reading frame of CNR1 (SEQ ID NO:13) corresponding to SEQ ID NOs: 14-22. In still another embodiment, the region is comprised within other regions in the open reading frame of CNR1. In yet another embodiment of a method according to the invention, the CB1 receptors in the human macrophages are knocked down at least about 60%, at least about 70%, at least about 75%, at least about 80%, at least about 85%, at least about 90%, at least about 95%, at least about 98%, at least about 99%, or about 100%.

In one or more of these embodiments, the glucan is β-1,3-D-glucan. In one or more embodiments, the siRNA is entrapped in shells of the glucan about 2-4 μm in diameter. In one or more of these embodiments, the siRNA is complexed with α-helical amphipathic peptide Endoporter (EP) prior to glucan encapsulation. This facilitates membrane interaction and endosomal escape of siRNA. Thus, in such an embodiment, there are three components of GeRPs: the siRNA, the glucan shell, and EP.

In one or more of these embodiments, the subject is suffering from type 2 diabetes mellitus. In related embodiments, the subject shows resistance to insulin, and/or the subject's beta cells are not functioning. In related embodiments, the subject is at risk for (developing) type 2 diabetes mellitus. In one or more of these embodiments, the subject is human. In certain embodiments, the methods disclosed herein can reverse beta cell loss (to exact a therapeutic effect) or can delay beta cell loss (to exact a prophylactic effect).

In one or more of these embodiments, the composition is administered orally or parenterally. In one or more of these embodiments, the composition further comprises a pharmaceutically acceptable carrier, a diluent, a penetration enhancer, an excipients, or combinations thereof.

In one aspect, the invention provides a method for in vivo knockdown of macrophage CB1 receptor, comprising contacting a macrophage with a composition comprising glucan-encapsulated siRNA, wherein the siRNA is directed against CNR1.

In another aspect, the invention provides a method of promoting the survival of pancreatic beta cells and/or the production of insulin by pancreatic beta cells in a subject suffering from type 2 diabetes mellitus or at risk for type 2 diabetes mellitus, comprising administering to the subject a composition comprising glucan-encapsulated siRNA, wherein the siRNA is directed against CNR1.

In one aspect, the invention provides a composition comprising glucan-encapsulated siRNA, wherein the siRNA is directed against a region of CNR1, wherein the region is comprised within the open reading frame of CNR1 (SEQ ID NO:13) corresponding to SEQ ID NOs: 14-22, for use in the treatment of type 2 diabetes mellitus in a human subject.

In one or more of these embodiments, the region of CNR1 is that region of the gene for which knockdown of the receptors upon macrophage uptake of siRNA is most effective. In related embodiments, the siRNA is directed against a region of the gene encoding the CB1 receptor, wherein the CB1 receptors in the macrophages are knocked down at least about 60%, at least about 70%, at least about 75%, at least about 80%, at least about 85%, at least about 90%, at least about 95%, at least about 98%, at least about 99%, or about 100%.

In another embodiment of a composition according to the invention, the glucan is β-1,3-D-glucan. In related embodiments, the siRNA is entrapped in shells of the glucans about 2-4 µm in diameter. In still another embodiment, the siRNA is complexed with α-helical amphipathic peptide EP prior to glucan encapsulation.

In certain embodiments, the compositions disclosed herein can reverse beta cell loss (to exact a therapeutic effect) or can delay beta cell loss (to exact a prophylactic effect) following administration to a subject in need of such therapy or prophylaxis.

In another aspect, the invention provides a composition comprising glucan-encapsulated siRNA, wherein the siRNA is directed against a region of CNR1, wherein the region is comprised within the open reading frame of CNR1 (SEQ ID NO:13) corresponding to SEQ ID NOs: 14-22, for in vivo knockdown of macrophage CB1 receptor in a human subject suffering from, or at risk for developing, type 2 diabetes mellitus. The macrophages can be phagocytic macrophages. In another embodiment, the siRNA is directed against a region of CNR1 that corresponds to those regions identified herein as effective targets in the rat $CB_1R$-encoding gene (cnr1).

Another aspect of the invention is a composition comprising glucan-encapsulated siRNA directed against a region of cannabinoid receptor 1 (CNR1). In one or more embodiments, the siRNA comprises a sense strand and an antisense strand, wherein the antisense strand is a RNA sequence at least 90% complementary to a CNR1 cDNA sequence selected from the group consisting of SEQ ID NOs:14-22, for use in the treatment of type 2 diabetes mellitus in a subject.

One embodiment provides a composition comprising glucan-encapsulated siRNA directed against a region of CNR1, wherein the region is comprised within the open reading frame of CNR1 (SEQ ID NO:13) corresponding to SEQ ID NOs: 14-22, for in vivo knockdown of macrophage CB1 receptor in a human subject suffering from or at risk for type 2 diabetes mellitus.

Another embodiment provides the use of a composition comprising glucan-encapsulated siRNA directed against a region of CNR1, wherein the region is comprised within the open reading frame of CNR1 (SEQ ID NO:13) corresponding to SEQ ID NOs: 14-22 in the preparation of a medicament for the treatment of type 2 diabetes mellitus.

Another embodiment provides the use of a composition comprising glucan-encapsulated siRNA directed against a region of CNR1, wherein the region is comprised within the open reading frame of CNR1 (SEQ ID NO:13) corresponding to SEQ ID NOs: 14-22 in the preparation of a medicament for in vivo knockdown of macrophage CB1 receptor in a human subject suffering from or at risk for type 2 diabetes mellitus.

In one or more embodiments, the compound consists of between 5 and 40 nucleotides, comprising a nucleotide sequence at least 90% complementary to a contiguous portion of SEQ ID NO:13, as measured over the entire length of the compound, encapsulated in a glucan.

In one or more embodiments, the oligonucleotide is a single-stranded oligonucleotide. In one or more embodiments, the oligonucleotide is a DNA oligonucleotide.

In one or more embodiments, the oligonucleotide is a RNA oligonucleotide. In one or more embodiments, the compound is a short interfering RNA (siRNA) molecule wherein the siRNA comprises a sense strand having the sequence of SEQ ID NO:9 and an antisense strand having the sequence of SEQ ID NO:10. In one or more embodiments, compound is 100% complementary to a contiguous portion of SEQ ID NO:13, as measured over the entire length of said compound.

In one or more embodiments, the compound comprises at least one nucleotide selected from the group consisting of adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, and inosine.

In one or more embodiments, the compound is complexed with α-helical amphipathic peptide Endoporter (EP).

In one or more embodiments, the compound is siRNA complexed with α-helical amphipathic peptide Endoporter (EP) and encapsulated in a glucan. In certain embodiments, the glucan is β-1,3-D-glucan.

In one or more embodiments, the compound is 20, 21, 22, 23, 24, 25, 26, 27, 28, 29, or 30 nucleotides in length.

One aspect of the invention provides a pharmaceutical composition comprising the compound of claim 20 and an ingredient selected from the group consisting of a pharmaceutically acceptable carrier, a diluent, a penetration enhancer, an excipients, and combinations thereof.

In one or more embodiments, the compound is a pharmaceutically acceptable salt. In certain embodiments, the salt is a sodium salt.

Other aspects of the invention are described in or are obvious from the following disclosure and are within the ambit of the invention.

BRIEF DESCRIPTION OF THE DRAWINGS

The following Detailed Description, given by way of Examples, but not intended to limit the invention to specific embodiments described, may be understood in conjunction with the accompanying figures, in which:

FIG. 1a provides two bar graphs and a point plot showing that chronic oral treatment with JD5037, a highly potent, selective and peripherally restricted $CB_1R$ inverse agonist, has no effect on body weight and adiposity (bar graphs) and causes a small reduction in food intake (point plot) compared to vehicle-treated ZDF rats. FIG. 1b provides four bar graphs showing that in the same ZDF rats, JD5037 treatment reverses the increase in hepatic triglycerides, plasma ALT, and hepatic FAS and SCD-1 mRNA levels to or near levels in lean controls. FIG. 1C provides four bar graphs showing that JD5037 treatment of the same ZDF rats normalizes fasting blood glucose and HbA1c and causes a further increase in plasma insulin and c-peptide levels; n=12 rats/group. FIG. 1d provides three bar graphs showing that JD5037 does not reverse global insulin resistance but slightly improves peripheral glucose uptake, as assessed in euglycemic-hyperinsulinemic clamps; n=5/group. Columns (or points) and vertical bars represent means±SEM from 20 animals/group; *P<0.05,  P<0.01, *P<0.001.

FIG. 3a provides immunohistochemical identification of insulin, Tunel-positive cells and $CB_1R$ protein was carried out in pancreatic islets from lean rats (open columns) and ZDF rats treated with vehicle (gray columns) or JD5037 for 4 weeks (black columns). The bar graphs show insulin and $CB_1R$ mRNA levels and anandamide (AEA) content of whole pancreas, or they show the percentage of Tunel-positive cells; n=15 rats/group. Significant difference from lean control, *P<0.05, ***P<0.001. FIG. 3b shows, in bar graph form, glucose-induced insulin and c-peptide release, determined as described in the Examples section, below, in intact rats (left and middle bar graphs) or in isolated islets (right bar graph) from lean (open columns), vehicle-treated ZDF (gray columns), or JD5037-treated ZDF rats (black columns). In the left and middle bar graphs, the column indicates the glucose-induced increase in plasma insulin or c-peptide, respectively, over baseline insulin levels shown in gray scale; n=10 rats or 8 islet preparations/group; *P<0.05, **P<0.01, P<0.001 relative to value in corresponding group on 0.5 g/L glucose. FIG. 3c shows, in bar graph form, Glut2 and glucokinase mRNA levels in pancreata from lean or from vehicle- or JD5037-treated ZDF rats; n=10 preparations/group; Significance as in FIG. 3a. FIG. 3d shows baseline blood glucose (point plot), insulin (bar graph), and c-peptide (bar graph) levels in prediabetic 6-week-old ZDF rats and their biweekly change during 12 weeks of daily treatment with vehicle—(gray columns in bar graphs, solid circles in point plot) or JD5037 (black columns in bar graphs, solid triangles in point plot). Values in age-matched lean controls are shown by open symbols; n=10 rats/group during weeks 6-18. Significant difference from corresponding value in lean (*, or *), or vehicle-treated ZDF rats (#,## or ###).

FIG. 5a shows bar graph quantitation results of immunohistochemical staining indicating infiltration of diabetic islets by CD68+ macrophages and upregulation of the Nlrp3 inflammasome prevented by 28-day JD5037 treatment. FIG. 5b provides five bar graphs indicating that increases in pro-inflammatory and decreases in anti-inflammatory gene expression in the diabetic pancreas are reversed by JD5037 treatment. FIG. 5c provides nine bar graphs showing that upregulation of Nlrp3 target genes, IL-1R, and Txnip in diabetic pancreas is reversed by JD5037 treatment. Eight week-old ZDF rats were treated for 28 days orally with vehicle (gray columns) or JD5037 (3 mg/kg/day, black columns), with age-matched lean controls (open columns) serving as reference; n=20 animals/group, statistics as for FIG. 1.

FIG. 8b shows the effect of clodronate treatment on glycemic control and reverses inflammatory cell infiltration by clodronate treatment, decreases $CB_1R$ and Nlrp3, and increases insulin expression both at protein (point plot and bar graphs, FIG. 8a) and mRNA levels (bar graphs, FIG. 8b).

Figure 1:
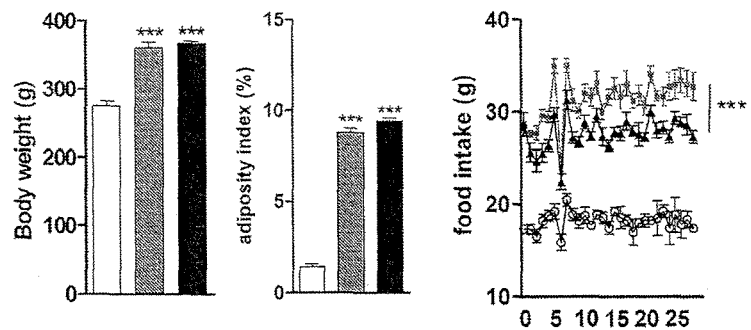
FIG. 1 shows that peripheral $CB_1R$ blockade causes weight-independent improvements in steatosis and glycemic control in ZDF rats. Eight-week-old male ZDF rats were treated daily for 28 days by oral gavage with 3 mg/kg JD5037 (black columns or triangles) or vehicle (gray columns, squares). Open columns and open circles depict corresponding values in lean control rats.
Figure 1:
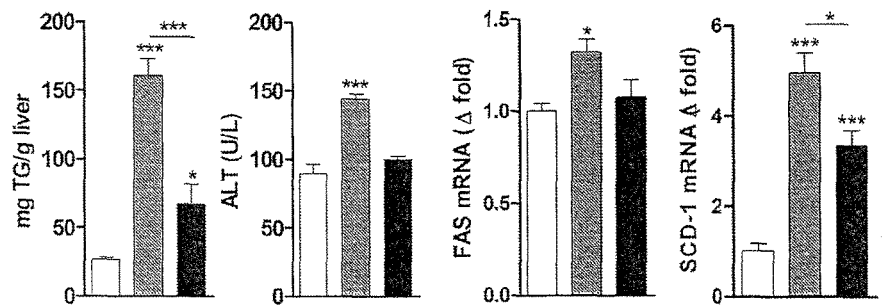
Figure 1:
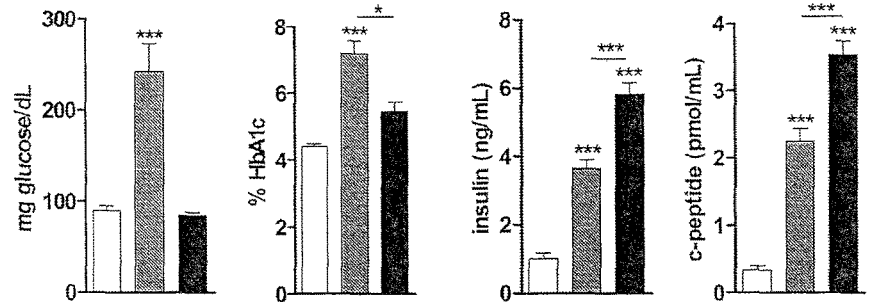
Figure 1:
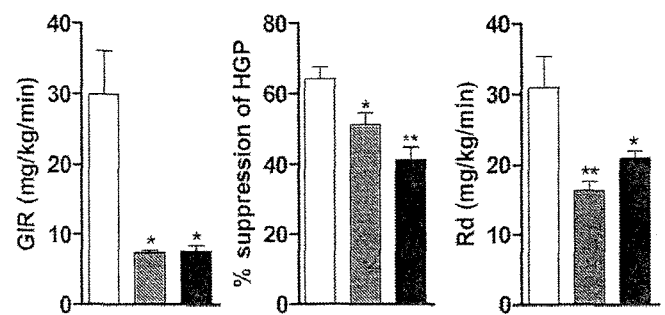

Clodronate reverses increased TNFα and MCP-1 expression. Glycemic control was monitored for 20 days in lean controls (open columns, bar graphs/open circles, point plot FIG. 8a), ZDF rats treated with empty liposomes (gray columns, bar graphs/squares, point plot FIG. 8a) or clodronate-treated ZDF rats (black columns, bar graphs/triangles, point plot FIG. 8a), with mRNA and protein levels of the indicated genes determined following sacrificing the animals at the end of the 20-day treatment period. Macrophages were depleted in 8 week-old ZDF rats (8 animals/group) by 3 successive injections of clodronate-containing liposomes at 2-day intervals, as described in the Examples, below. Columns and bars represent means±SEM from 8 rats/group, statistics as for FIG. 1.

Figure 9:
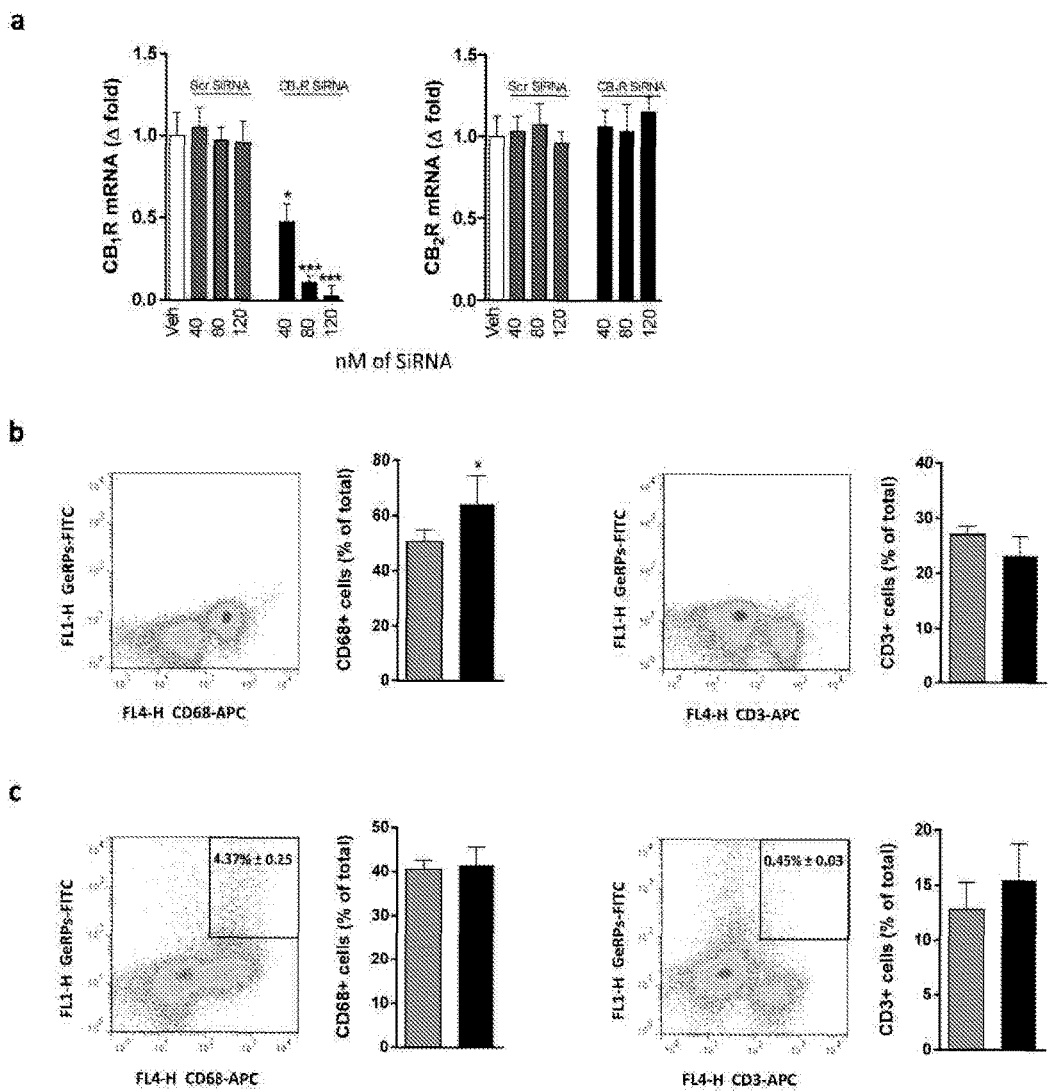

FIG. 9 shows the specificity of $CB_1R$ silencing by siRNA (labeled "siRNA" throughout FIG. 9) in macrophages. $CB_1R$ silencing by siRNA is specific, and the GeRPs (glucan-encapsulated siRNA particles) are specifically found in macrophages and not in monocytes or lymphocytes. FIG. 9a shows, in bar graph form, thioglycollate-induced peritoneal elicited macrophages (PEC) treated 48 h with 40, 80 or 120 nM of either scrambled siRNA (gray columns) or $CB_1R$ siRNA (black columns). $CB_1R$ mRNA expression was assessed by RT-qPCR. Columns and bars represent means±SEM from 4 independent experiments; *P<0.05. FIG. 9b shows FACS plots (and bar graph quantitation) for isolated leukocytes from GeRPs-treated ZDF rats analyzed by FACS after staining for CD68 and CD3 proteins. No GeRPs-positive cells were detected, and the numbers of cells were comparable between Scramble and $CB_1R$ SiRNA groups. FIG. 9c shows FACS plots (and bar graph quantitation) for PEC from GeRPs-treated ZDF rats analyzed by FACS after staining for CD68 and CD3 proteins, where only CD68-positive cells (macrophages) were also FITC-positive (GeRPS). The numbers of CD3+ and CD68+ cells were comparable among the 2 treatments. Blood and PEC from scramble GeRPs (gray columns) and $CB_1R$-GeRPs-treated ZDF rats (black columns) were collected after 9 and 10 days of treatment, respectively. Columns and bars represent means±SEM from 6 animals/group; *P<0.05.

Figure 10:
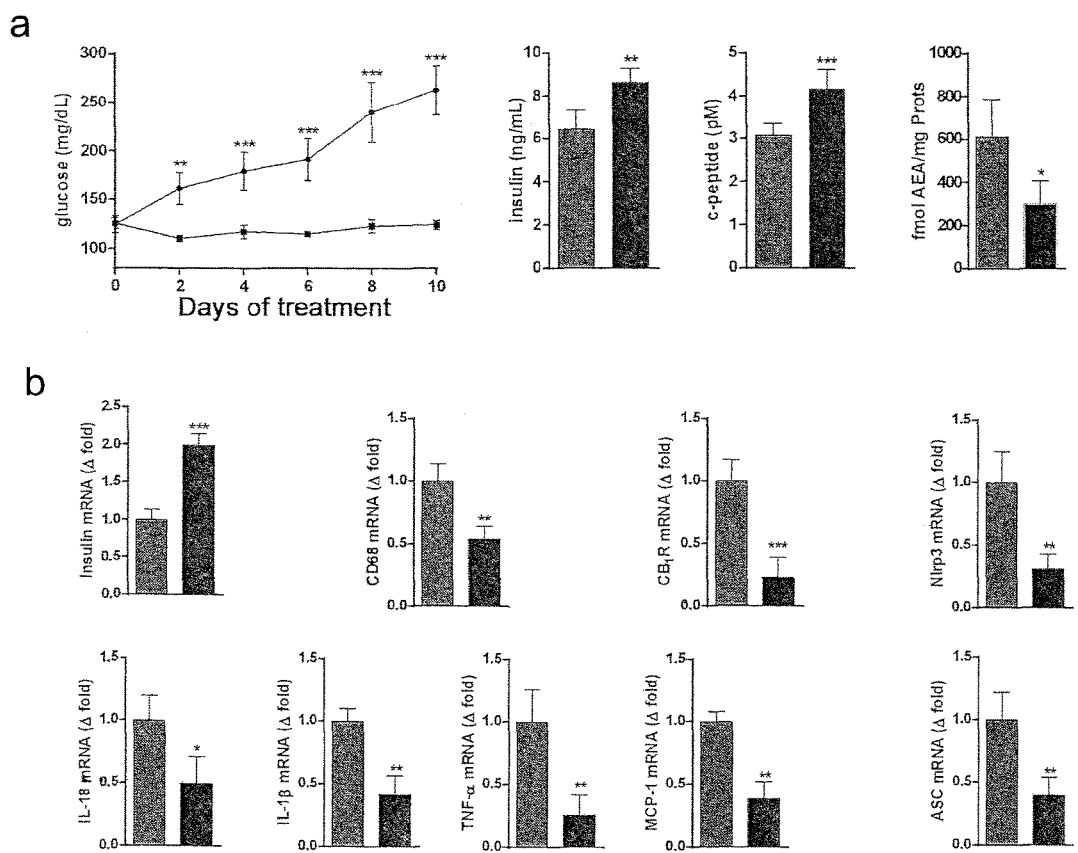

FIG. 10 shows that macrophage-selective siRNA-knockdown of $CB_1R$ in ZDF rats prevents hyperglycemia, macrophage infiltration and proinflammatory changes in pancreatic islets. FIG. 10a depicts, in point plot and bar graph form, baseline blood glucose in 8-week-old ZDF rats during 10 days of treatment with scrambled siRNA (gray columns, bar graphs, solid circles of point plot) or $CB_1R$ siRNA (black columns, bar graphs, solid squares of point plot). Plasma insulin, c-peptide, and pancreatic anandamide levels are quantified at end of treatment. FIG. 10b shows the quantitation in bar graph form of the results of immunohistochemical staining in which $CB_1R$ siRNA treatment increases islet insulin and reverses macrophage infiltration and decreases $CB_1R$ and Nlrp3 protein and mRNA n=6-8 independent experiments, statistics as for FIG. 1. siRNA treatment also reduces IL-1β, IL-18, TNF-α, MCP-1, and ASC expression in ZDF pancreas, n=6/group, means±SE are shown.

FIG. 11 illustrates how anandamide-induced β-cell apoptosis is induced via inflammasome activation in infiltrating macrophages. FIG. 11a shows, in point plots, that anandamide (AEA) activates the Nlrp3 inflammasome and its downstream targets in RAW264.7 macrophages, but not in MIN6 insulinoma cells. Cells were incubated for 4 h with vehicle or the concentrations of AEA indicated on the X-axis, followed by gene expression analyses using mRNA extracted from cells or analyses of secreted cytokines in the culture medium.

Figure 11A:
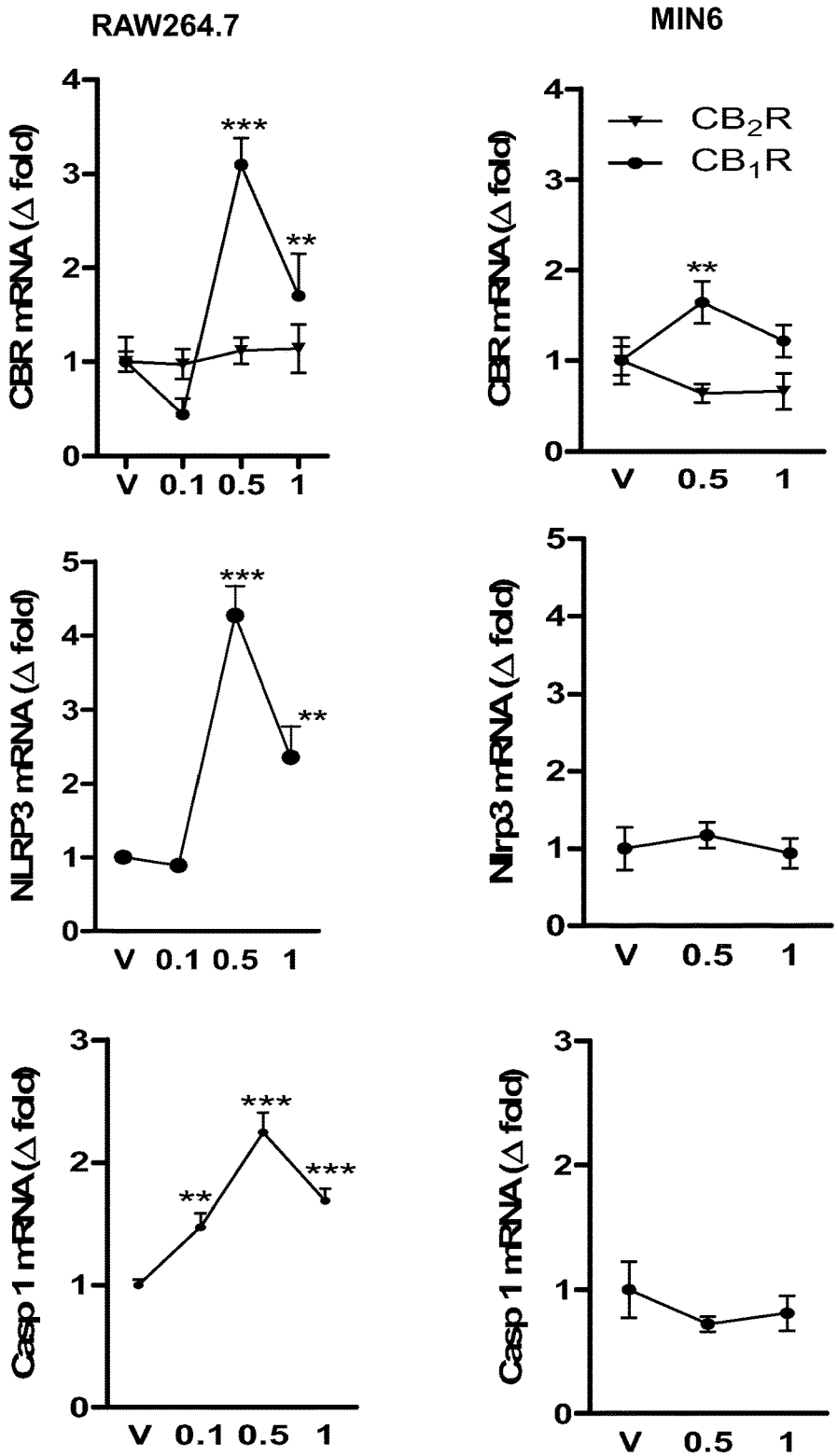
Figure 11A:
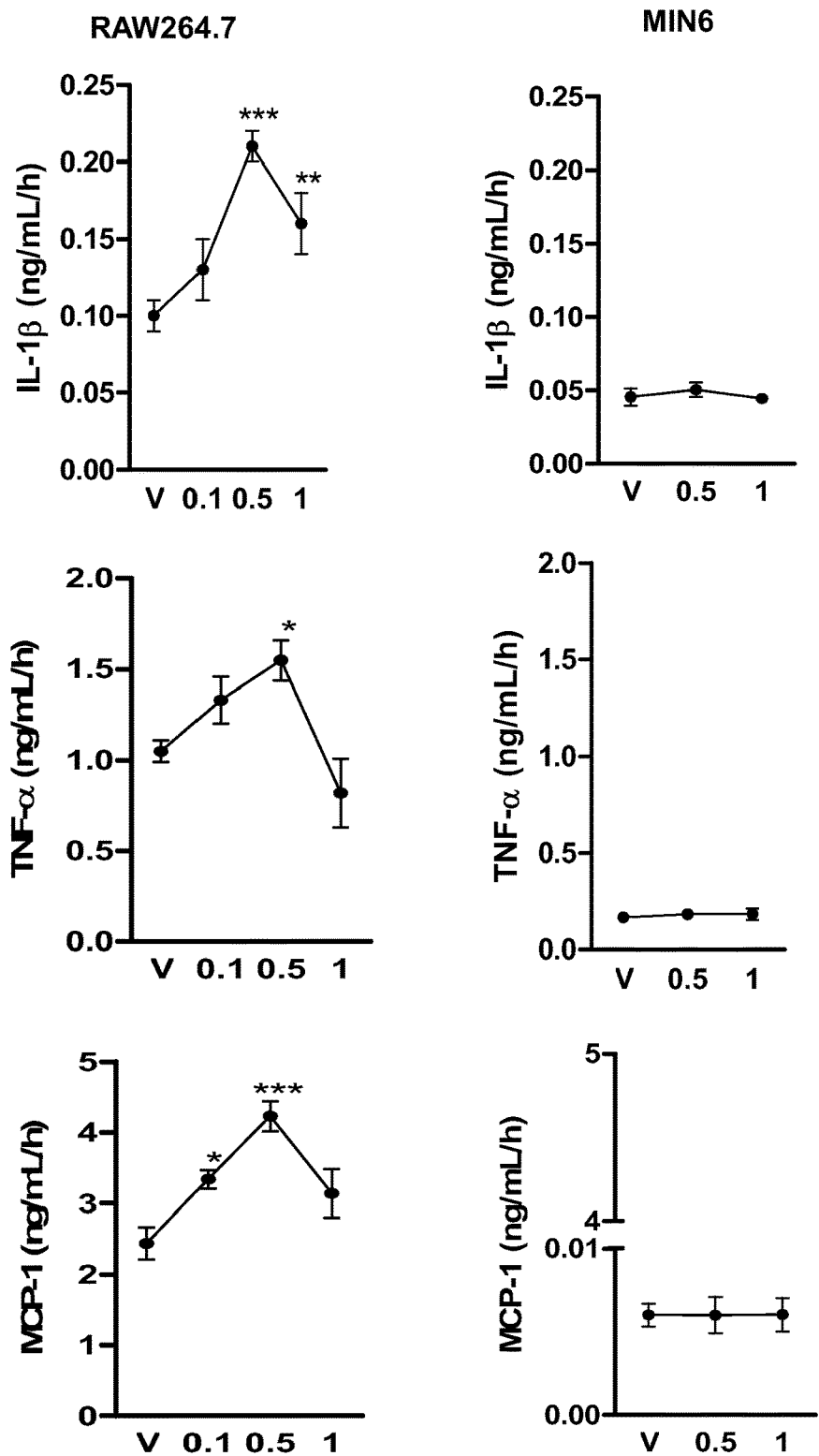
Figure 11B:
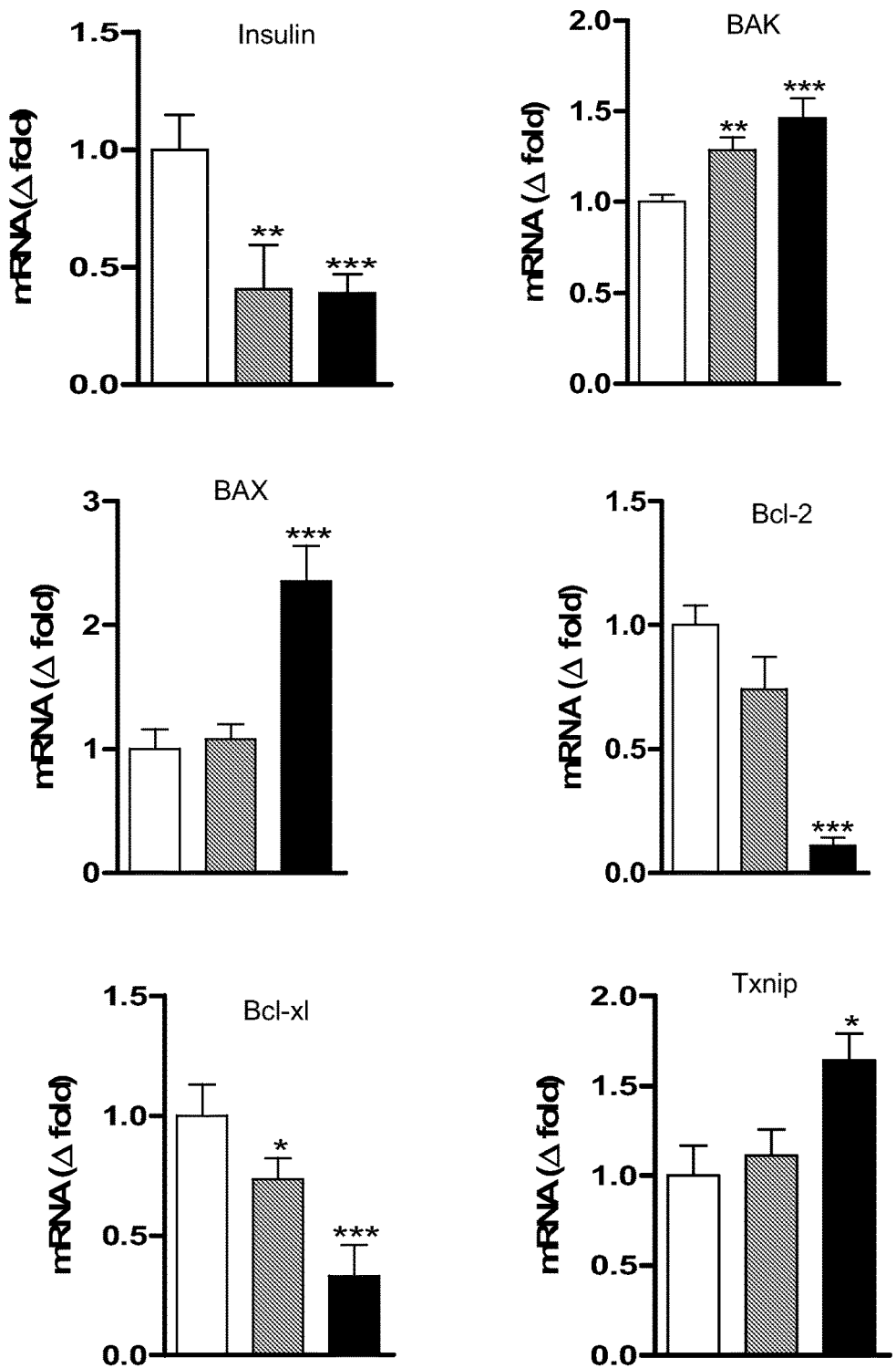

FIG. 11b shows, in bar graph form, that IL-1β is more efficacious than anandamide (AEA) in inducing β-cell apoptosis. MIN6 cells were incubated with maximally effective concentrations of AEA (0.5 nM) or IL-1β (30 ng/mL), followed by analyses of the expression of the indicated genes. IL-1β treatment (black bars), vehicle (white bars), IL-1R antagonist AEA (grey bars). Points/columns and vertical bars represent means±SEM from 6-8 independent experiments, statistics as in FIG. 1.

Figure 11C:
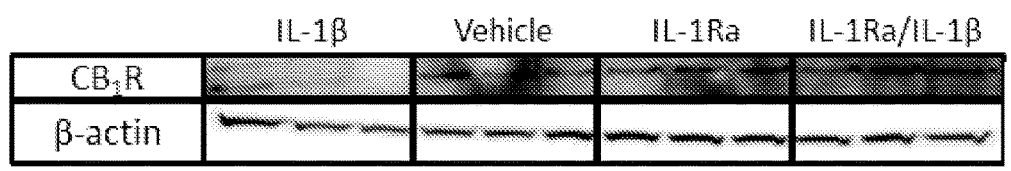
Figure 11C:
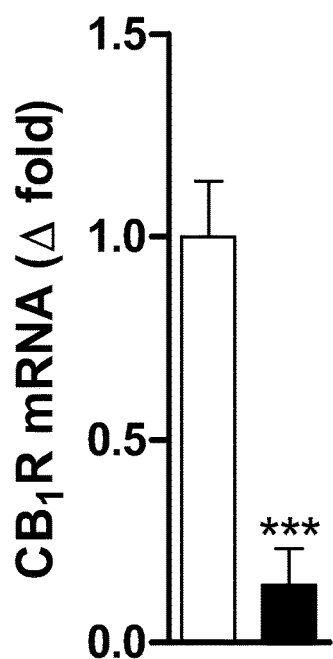
Figure 11C:
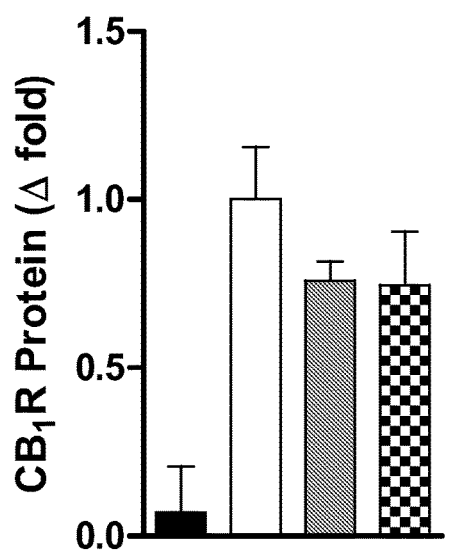

FIG. 11c shows a bar graph quantitation illustrating that IL-1β down-regulates $CB_1R$ mRNA and protein expression in MIN6 cells via the IL-1R, as indicated by blockade of this effect by IL-1R antagonist (10 ng/mL). IL-1β treatment (black bar), vehicle (white bar), IL-1R antagonist AEA (grey bar), and co-treatment IL-1β and IL-4Ra (black squares bar).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 2, 2011, 18.4 KB, which is incorporated by reference herein. In the accompanying sequence listing:

SEQ ID NO: 1 is the nucleotide sequence of rat CB1R gene (cnr1) publicly available (NCBI Gene ID 25248, NM_012784.4).

SEQ ID NO: 2 is the protein sequence of the rat receptor (NP_036916.1).

SEQ ID NO: 3 is the nucleotide sequence of the human CB1R gene (CNR1) sequence (NCBI Gene ID 1268, NM_001160226.1).

SEQ ID NO: 4 is the protein sequence of the human CB1 receptor (NP_001153698.1).

SEQ ID NOs: 5-12 are the nucleotide sequences of RNA oligonucleotides, used in siRNA testing of the methods of the invention as described in detail below.

SEQ ID NO: 13 is the nucleotide sequence of the open reading frame of the human cannabinoid receptor 1 (brain) (NM_016083.4).

SEQ ID NOs: 14-22 are nucleotide sequences of regions of the open reading frame of the human cannabinoid receptor identified as described below and set forth specifically in Table 4 of this disclosure.

DETAILED DESCRIPTION

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

Definitions

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices, and materials are now described.

As used in this application, including the appended claims, the singular forms "a," "an," and "the" include plural references, unless the content clearly dictates otherwise, and are used interchangeably with "at least one" and "one or more." Thus, reference to "a polynucleotide" includes a plurality of polynucleotides or genes, and the like.

As used herein, the term "about" represents an insignificant modification or variation of the numerical value, such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

Reference herein to any numerical range (for example, a dosage range) expressly includes each numerical value (including fractional numbers and whole numbers) encompassed by that range. For example, reference herein to a range of "less than x" (wherein x is a specific number) includes whole numbers x−1, x−2, x−3, x−4, x−5, x−6, etc., and fractional numbers x−0.1, x−0.2, x−0.3, x−0.4, x−0.5, x−0.6, etc. In yet another illustration, reference herein to a range of from "x to y" (wherein x is a specific number, and y is a specific number) includes each whole number of x, x+1, x+2 . . . to y−2, y−1, y, as well as each fractional number, such as x+0.1, x+0.2, x+0.3 . . . to y−0.2, y−0.1. In another example, the term "at least 95%" includes each numerical value (including fractional numbers and whole numbers) from 95% to 100%, including, for example, 95%, 96%, 97%, 98%, 99% and 100%.

As used herein, the terms "oligonucleotide," "siRNA," "siRNA oligonucleotide," and "siRNAs" are used interchangeably throughout the specification and include linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hoogsteen types of base pairing, or the like.

In the present context, the terms "nucleotide" covers naturally occurring nucleotides as well as non-naturally occurring nucleotides. It should be clear to the person skilled in the art that various nucleotides which previously have been considered "non-naturally occurring" have subsequently been found in nature. Thus, "nucleotide" includes not only the known purine and pyrimidine heterocycles, but also heterocyclic analogues and tautomers thereof. Illustrative examples of nucleotides are adenine, guanine, thymine, cytosine, uracil, purine, xanthine, diaminopurine, 8-oxo-$N_6$-methyladenine, 7-deazaxanthine, 7-deazaguanine, $N_4,N_4$-ethanocytosin, $N_6,N_6$-ethano-2,6-diaminopurine, 5-methylcytosine, 5-($C_3$-$C_6$)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner, et al., U.S. Pat. No. 5,432,272. The term "nucleotide" is intended to cover all of these examples as well as analogues and tautomers thereof. Especially interesting nucleotides are adenine, guanine, thymine, cytosine, and uracil, which are considered as the naturally occurring nucleotides in relation to therapeutic and diagnostic application in humans.

The term nucleotide further includes 2'-deoxy and 2'-hydroxyl forms, e.g., as described in Kornberg and Baker, DNA Replication, 2nd Ed. (Freeman, San Francisco, 1992).

"Analogs" in reference to nucleotides include synthetic nucleotides having modified base moieties and/or modified sugar moieties. Such analogs include, for example, synthetic nucleotides designed to enhance binding properties.

As used herein, the term "downstream" when used in reference to a direction along a nucleotide sequence means in the direction from the 5' to the 3' end. Similarly, the term "upstream" means in the direction from the 3' to the 5' end.

As used herein, the term "gene" means the gene and all currently known variants thereof and any further variants which may be elucidated.

As used herein, a "variant" of a polypeptide refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity (i.e., binding a target sequence) may be found using computer programs well known in the art, for example, LASERGENE™ software (DNASTAR™).

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

As used herein, the term "mRNA" means the presently known mRNA transcript(s) of a targeted gene, and any further transcripts which may be elucidated.

RNA interference (RNAi) is a sequence-specific RNA degradation process that provides a relatively easy and direct way to knock down, or silence, theoretically any gene. In naturally occurring RNAi, a double-stranded RNA (dsRNA) is cleaved by an RNase III/helicase protein, Dicer, into small interfering RNA (siRNA) molecules, a dsRNA of 19-27 nucleotides (nt) with 2-nt overhangs at the 3' ends. These siRNAs are incorporated into a multicomponent-ribonuclease called RNA-induced silencing complex (RISC). One strand of siRNA remains associated with RISC and guides the complex toward a cognate RNA that has sequence complementary to the guider ss-siRNA in RISC. This siRNA-directed endonuclease digests the RNA, thereby inactivating it. Recent studies have revealed that chemically synthesized 21-27-nt siRNAs exhibit RNAi effects in mammalian cells, and the thermodynamic stability of siRNA hybridization (at terminals or in the middle) plays a central role in determining the molecule's function.

Thus, RNA interference "RNAi" is mediated by double-stranded RNA (dsRNA) molecules that have sequence-specific homology to a "target" nucleic acid sequence. According to the present invention, siRNA molecules are used. Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 5 to about 50 nucleotides (nt). In examples of non-limiting embodiments, siRNAs can comprise about 5 to about 40 nt, about 5 to about 30 nt, about 10 to about 30 nt, about 15 to about 25 nt, or about 20-25 nucleotides.

Selection of appropriate RNAi is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of RNAi that exhibit a high degree of complementarity to target nucleic acid sequence in a subject to be controlled and a lower degree of complementarity to corresponding nucleic acid sequences in other species.

The term, "complementary" means that two sequences are complementary when the sequence of one can bind to the sequence of the other in an anti-parallel sense, wherein the 3'-end of each sequence binds to the 5'-end of the other sequence and each A, T(U), G, and C of one sequence is then aligned with a T(U), A, C, and G, respectively, of the other sequence. Normally, the complementary sequence of the oligonucleotide has at least about 80%, about 85%, about 90%, about 95%, or about 100% complementarity to a defined sequence. Preferably, alleles or variants thereof can be identified. A BLAST program also can be employed to assess such sequence identity.

The term "complementary sequence" as it refers to a polynucleotide sequence relates to the base sequence in another nucleic acid molecule by the base-pairing rules. More particularly, the term or like term refers to the hybridization or base pairing between nucleotides or nucleic acids, such as, for instance, between the two strands of a double-stranded DNA molecule or between an oligonucleotide primer and a primer binding site on a single-stranded nucleic acid to be sequenced or amplified. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 95% of the nucleotides of the other strand, usually at least about 98%, and more preferably from about 99% to about 100%. Complementary polynucleotide sequences can be identified by a variety of approaches including use of well-known computer algorithms and software, for example, the BLAST program.

The term "target nucleic acid" refers to a nucleic acid to which the oligonucleotide is designed to specifically hybridize, e.g., a nucleic acid encoding CB1R. The target nucleic acid has a sequence that is complementary to the nucleic acid sequence of the corresponding oligonucleotide, e.g., siRNA, directed to the target. The term target nucleic acid may refer to the specific subsequence of a larger nucleic acid to which the oligonucleotide is directed or to the overall sequence (e.g., gene or mRNA) whose expression level it is desired to affect. In other words, the sequence of the interfering RNA (e.g., siRNA) can correspond to the full-length target gene or to a subsequence thereof.

As used herein, a "pharmaceutically acceptable" component/carrier is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a composition which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a composition effective to yield the desired therapeutic response. For example, an amount effective to delay the onset or worsening of type 2 diabetes mellitus. The specific safe and effective amount or therapeutically effective amount will vary with such factors as the severity of the condition, e.g., type 2 diabetes mellitus, being treated, the physical condition of the patient, the type of mammal or animal being treated, the duration of the treatment, the nature of concurrent therapy (if any), and the specific formulations employed.

A "heterologous" component refers to a component that is introduced into or produced within a different entity from that in which it is naturally located. For example, a polynucleotide derived from one organism and introduced by genetic engineering techniques into a different organism is a heterologous polynucleotide that, if expressed, can encode a heterologous polypeptide. Similarly, a promoter or enhancer that is removed from its native coding sequence and operably linked to a different coding sequence is a heterologous promoter or enhancer.

A "promoter," as used herein, refers to a polynucleotide sequence that controls transcription of a gene or coding sequence to which it is operably linked. A large number of promoters, including constitutive, inducible and repressible promoters, from a variety of different sources, are well known in the art and are available as or within cloned polynucleotide sequences (from, e.g., depositories such as the ATCC as well as other commercial or individual sources).

An "enhancer," as used herein, refers to a polynucleotide sequence that enhances transcription of a gene or coding sequence to which it is operably linked. A large number of enhancers, from a variety of different sources are well known in the art and available as or within cloned polynucleotide sequences (from, e.g., depositories such as the ATCC as well as other commercial or individual sources). A number of polynucleotides comprising promoter sequences (such as the commonly-used CMV promoter) also comprise enhancer sequences.

"Operably linked" refers to a juxtaposition, wherein the components so described are in a relationship permitting them to function in their intended manner. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within, or downstream of coding sequences. A polyadenylation sequence is operably linked to a coding sequence if it is located at the downstream end of the coding sequence.

"Gene delivery," "gene transfer," and the like, as used herein, are terms referring to the introduction of an exogenous polynucleotide (sometimes referred to as a "transgene products") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of gene products to mammalian cells, as is known in the art and described herein.

"In vivo" gene delivery, gene transfer, gene therapy, and the like, as used herein, are terms referring to the introduction of a vector comprising an exogenous polynucleotide directly into the body of an organism, such as a human or non-human mammal, whereby the exogenous polynucleotide is introduced to a cell of such organism in vivo.

A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

As used herein, a "target cell" or "recipient cell" refers to an individual cell or cells which is/are desired to be, or has/have been, a recipient of exogenous nucleic acid molecules, polynucleotides, and/or proteins. The term is also intended to include progeny of a single cell.

A "vector" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a coding sequence of interest in gene therapy. Vectors include, for example, viral vectors (such as adenoviruses ("Ad"), adeno-associated viruses (AAV), and retroviruses), liposomes and other lipid-containing complexes, and other macromolecular complexes capable of mediating delivery of a polynucleotide to a host cell. A glucan particle is described herein as a preferred vector. Vectors can also comprise other components or functionalities that further modulate gene delivery and/or gene expression, or that otherwise provide beneficial properties to the targeted cells.

As described and illustrated in more detail below, such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector, or vectors can be modified to provide such functionalities. A large variety of such vectors are known in the art and are generally available.

A "detectable marker gene" is a gene that allows cells carrying the gene to be specifically detected (e.g., distinguished from cells which do not carry the marker gene). A large variety of such marker gene products are known in the art. Preferred examples thereof include detectable marker gene products which encode proteins appearing on cellular surfaces, thereby facilitating simplified and rapid detection and/or cellular sorting. By way of illustration, the lacZ gene encoding beta-galactosidase can be used as a detectable marker, allowing cells transduced with a vector carrying the lacZ gene to be detected by staining.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "subject", "patient", and "individual", as used herein, interchangeably refer to a multicellular animal (including mammals (e.g., humans, non-human primates, murines, ovines, bovines, ruminants, lagomorphs, porcines, caprines, equines, canines, felines, ayes, etc.), avians (e.g., chicken), amphibians (e.g. *Xenopus*), reptiles, and insects (e.g. *Drosophila*). "Animal" includes guinea pig, hamster, ferret, chinchilla, mouse and cotton rat. The terms "subject", "patient", or "individual" refer to a mammalian subject to be treated, with human patients being preferred. In some cases, the methods of the invention find use in experimental animals, in veterinary application, and in the development of animal models for disease.

"Treatment" is an intervention performed with the intention of preventing the development or altering the pathology or symptoms of a disorder (e.g., type 2 diabetes mellitus 2 (T2DM)). Accordingly, "treatment" refers to both therapeutic treatment and prophylactic or preventative measures. "Treatment" may also be specified as palliative care. Those in need of treatment include those already with the disorder, as well as those in which the disorder is to be prevented.

The "treatment of type 2 diabetes mellitus" refers to an amount of a composition comprising siRNA, as described throughout the specification and in the Examples that follow, capable of invoking one or more of the following effects: (1) inhibition, to some extent, of T2DM, including, (i) slowing down of development of T2DM; (ii) reduction of T2DM, (iii) complete prevention of development of T2DM; (2) inhibition, to some extent, of at least one symptom of T2DM, including (i) reduction, (ii) slowing down or (iii) preventing the development of or providing the subject relief from one or more symptoms associated with T2DM.

Additional Embodiments of the Invention

According to the present invention, an siRNA oligonucleotide is designed to be specific for a gene, whose protein product either causes, participates in, or aggravates type 2 diabetes mellitus in a patient.

A fundamental property of oligonucleotides that underlies many of their potential therapeutic applications is their ability to recognize and hybridize specifically to complementary single-stranded nucleic acids employing either Watson-Crick hydrogen bonding (A-T and G-C) or other hydrogen bonding schemes such as the Hoogsteen/reverse Hoogsteen mode. Affinity and specificity are properties commonly employed to characterize hybridization characteristics of a particular oligonucleotide. Affinity is a measure of the binding strength of the oligonucleotide to its complementary target (expressed as the thermostability ($T_m$) of the duplex). Each nucleobase pair in the duplex adds to the thermostability and, thus, affinity increases with increasing size (No. of nucleosides) of the oligonucleotide. Specificity is a measure of the ability of the oligonucleotide to discriminate between a fully complementary and a mismatched target sequence. In other words, specificity is a measure of the loss of affinity associated with mismatched nucleotide pairs in the target.

The utility of an siRNA oligonucleotide for modulation (including inhibition) of an mRNA can be readily determined by simple testing. Thus, an in vitro or in vivo expression system comprising the targeted mRNA, mutations or fragments thereof, can be contacted with a particular siRNA oligonucleotide (synthesized using either standard or nuclease-resistant bonding), and levels of expression are compared to a control, that is, using the identical expression system that was not contacted with the siRNA oligonucleotide.

It is understood that the target to which siRNAs described herein are directed include allelic forms of the targeted gene and the corresponding mRNAs including splice variants. There is substantial guidance in the literature for selecting particular sequences for siRNA oligonucleotides, given a knowledge of the sequence of the target polynucleotide.

Where the target polynucleotide comprises a mRNA transcript, sequence-complementary oligonucleotides, e.g., siRNA, can hybridize to any desired portion of the transcript. Such oligonucleotides are, in principle, effective for inhibiting translation and capable of inducing the effects described herein. It is hypothesized that translation is most effectively inhibited by the mRNA at a site at or near the initiation codon. Thus, oligonucleotides complementary to the 5'-region of mRNA transcript are contemplated. Oligonucleotides complementary to the mRNA, including the initiation codon (the first codon at the 5' end of the translated portion of the transcript) or codons adjacent to the initiation codon are likewise contemplated.

In certain embodiments, the oligonucleotide, e.g., siRNA, is targeted to a translation initiation site (AUG codon) or sequences in the coding region, 5' untranslated region, or 3'-untranslated region of an mRNA. The functions of messenger RNA to be interfered with include all vital functions such as translocation of the RNA to the site for protein translation, actual translation of protein from the RNA, splicing or maturation of the RNA, and possibly even independent catalytic activity that may be engaged in by the RNA. The overall effect of such interference with the RNA function is to cause interference with protein expression.

A number of nucleotide and nucleoside modifications have been shown to make the oligonucleotide, e.g., siRNA, into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides containing at least one phosphorothioate modification are, for example, contemplated. In some cases, oligonucleotide modifications that enhance target binding affinity are also, independently, able to enhance nuclease resistance. Some desirable modifications can be found, for example, in De Mesmaeker et al. Acc. Chem. Res. 1995, 28:366-374.

Specific examples of contemplated oligonucleotides, e.g., siRNA, envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Additionally contemplated are amide backbones, morpholino backbone, peptide nucleic acid (PNA) backbone, polyamide backbone. Oligonucleotides may also comprise one or more substituted sugar moieties.

Oligonucleotides, e.g., siRNA, may also include, additionally or alternatively, nucleotide modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases. A "universal" base known in the art, e.g., inosine, may be included.

In another embodiment, the nucleic acid molecule, e.g., siRNA, described herein is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

Methods by which to transfect cells with RNAi vectors are well known in the art and include, but are not limited to, electroporation, particle bombardment, microinjection, transfection with viral vectors, transfection with retrovirus-based vectors, and liposome-mediated transfection. Any of the types of nucleic acids that mediate RNA interference can be synthesized in vitro using a variety of methods well known in the art and inserted directly into a cell. As mentioned above, RNAi molecules can be made through the well-known technique of solid-phase synthesis.

siRNA

The term "siRNA" used herein refers to a nucleic acid molecule mediating RNA interference or gene silencing. The siRNA to target (silence, reduce, and/or inhibit) expression of a gene (e.g., cnr1, CNR1) provides an effective gene knock-down method or gene therapy method.

In one embodiment, the siRNA molecule may consist of a sense RNA strand (comprising sequence corresponding to CB1R mRNA) and an antisense RNA strand (comprising sequence complementary to CB1R mRNA) and form a duplex structure. In another embodiment, the siRNA molecule may have a single strand structure comprising self-complementary sense and antisense strands.

In another embodiment, the siRNA molecule is not restricted to a RNA duplex of which two strands are completely paired and may comprise non-paired portion such as mismatched portion with non-complementary bases and bulge with no opposite bases. The overall length of the siRNA can then be longer than as described above.

The siRNA molecule may comprise either blunt or cohesive end(s), so long as it enables silencing, to some degree, the cnr1/CNR1 expression due to RNAi effect. The cohesive end may be prepared in 3'-end overhanging structure or 5'-end overhanging structure.

Small interfering RNA (siRNA) may be recombinantly produced, for example, from a genetically engineered system, or it may be a synthetic product, for example, produced by in vitro peptide synthesis or in vitro translation. They may be prepared via chemical synthesis, in vitro transcription, siRNA expression vectors, and PCR expression cassettes.

Thus, the oligonucleotides, e.g., siRNA, used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art.

siRNAs generally have a well characterized structure: a short (about 21 bp) double-stranded RNA (dsRNA) with phosphorylated 5' ends and hydroxylated 3' ends with two overhanging nucleotides. The Dicer enzyme catalyzes the production of siRNAs from longer dsRNAs and small hairpin RNAs, but siRNAs can also be introduced (for example, via transfection).

siRNAs may, in certain embodiments, comprise a double-stranded sequence of about 15 to about 60 nucleotides in length (e.g., about 15-60, 15-50, 15-40, 15-30, 15-25, or 19-25 nucleotides in length), wherein the siRNA molecule silences cnr1/CNR1 expression. In some embodiments, the siRNA molecule has 3' overhangs of one, two, three, four, or more nucleotides on one or both sides of the double-stranded region. In other embodiments, the siRNA molecule lacks overhangs (i.e., has blunt ends). Preferably, the siRNA molecule has 3' overhangs of two nucleotides on each side of the double-stranded region. Examples of 3' overhangs include, but are not limited to, 3' deoxythymidine (dT) overhangs of one, two, three, four, or more nucleotides.

Examples of siRNA include, without limitation, a double-stranded polynucleotide molecule assembled from two separate oligonucleotides, wherein one strand is the sense strand and the other is the complementary antisense strand; a double-stranded polynucleotide molecule assembled from a single oligonucleotide, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

siRNA design comprises, in one embodiment, the selection of target sequences of 21 nucleotides that begin with AA and are located within a region of the coding sequence that is within 50-100 nucleotides of the AUG start codon and within 50-100 nucleotides from the termination codon. The presence of AA at the start of the sequence allows for the use of dTdT at the 3'-end of the antisense sequence. The sense strand can also be synthesized with dTdT at the 3' end, because only the antisense strand is involved in target recognition. The use of dTdT reduces the cost of synthesis and also makes the siRNA duplex more resistant to exonuclease activity. Target sequences also begin with other nucleotide pairs (in additional embodiments).

Once a target sequence has been chosen, a BLAST search is initiated to ensure that the target sequence is not homologous to other gene sequences. In one embodiment, target sequences that have more than 15 contiguous bases pairs of homology to other genes in the NCBI database are eliminated.

Once a potential siRNA sequence has been identified, the sequence can be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., boz094.ust.hk/RNAi/siRNA. One of skill in the art will appreciate that sequences with one or more of the foregoing characteristics may be selected for further analysis and testing as potential siRNA sequences. siRNA sequences complementary to the siRNA target sites may also be designed.

Additionally, potential siRNA target sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal foldback structures. However, one of skill in the art will appreciate that sequences with one or more of the foregoing characteristics may still be selected for further analysis and testing as potential siRNA sequences.

In some embodiments, potential siRNA target sequences may be further analyzed based on siRNA duplex asymmetry. In other embodiments, potential siRNA target sequences may be further analyzed based on secondary structure at the mRNA target site. For example, mRNA secondary structure can be modeled to select siRNA sequences which favor accessibility at the mRNA target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs can also provide an indication of whether the sequence may be immunostimulatory. Once an siRNA molecule is found to be immunostimulatory, it can then be modified to decrease its immunostimulatory properties. As a non-limiting example, an siRNA sequence can be contacted with a mammalian responder cell under conditions such that the cell produces a detectable immune response to determine whether the siRNA is an immuno-stimulatory or a non-immunostimulatory siRNA. The mammalian responder cell may be from a naive mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, TNF-β, IFN-α, IFNγ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 20% of the nucleotides in the siRNA duplex can be replaced with modified nucleotides such as 2'OMe nucleotides. The modified siRNA can then be contacted with a mammalian responder cell as described above to confirm that its immunostimulatory properties have been reduced or abrogated.

According to one preferred embodiment of the invention, the nucleotides in the siRNA may be modified to provided higher specificity and affinity for a target mRNA. For example nucleotides may be substituted with LNA monomers, which can be in contiguous stretches or in different positions. The modified siRNA preferably has a higher association constant (Ka) for the target sequences than the complementary sequence. Binding of the modified or non-modified siRNAs to target sequences can be determined in vitro under a variety of stringency conditions using hybridization assays.

In certain instances, the siRNA molecule comprises at least one modified nucleotide in the sense and/or antisense of the sequence. As a non-limiting example, the siRNA molecule can be selectively modified at less than about 20% of the nucleotides in the sequence. Preferably, the modified siRNA molecule is notably less immunostimulatory than a corresponding unmodified siRNA sequence and is capable of silencing expression of the target sequence.

According to one embodiment, the peripherally restricted (non-brain-penetrant) $CB_1R$ inverse agonist, JD5037 ((S)-2-((S,E)-3-(4-chlorophenyl)-N'-((4-chlorophenyl)sulfonyl)-4-phenyl-4,5-dihydro-1H-pyrazole-1-carboximidamido)-3-methylbutanamide), was synthesized as described in Tam, et al. 2012 *Cell Metab* 16, 167-179, as well as in Chorvat, et al. 2012 *Bioorg Med Chem Lett* 22:6173-6180.

The siRNA described herein can be chemically synthesized or may be encoded by a plasmid (e.g., transcribed as sequences that automatically fold into duplexes with hairpin loops). siRNA can also be generated by cleavage of longer dsRNA (e.g., dsRNA greater than about 25 nucleotides in length) with the *E coli* RNase III or Dicer. These enzymes process the dsRNA into biologically active siRNA.

"Synthesized," as used herein and is understood in the art, refers to purely chemical, as opposed to enzymatic, methods for producing polynucleotides. "Wholly" synthesized DNA sequences are, therefore, produced entirely by chemical means, and "partially" synthesized DNAs embrace those wherein only portions of the resulting DNA were produced by chemical means.

In one embodiment, the invention employs purified and isolated CB1R siRNA oligonucleotides. The invention also embraces oligonucleotides that have at least about 99%, at least about 98%, at least about 97%, at least about 95%, or at least about 90% identity and/or homology to the CB1R siRNA oligonucleotides. Percent sequence "identity" or "homology" with respect to the preferred CB1R siRNA oligonucleotides is defined herein as the percentage of nucleotides in the candidate sequence that are identical with those in the CB1R siRNA oligonucleotide sequence. In an additional embodiment, the percentage is calculated after aligning both sequences and introducing gaps, if necessary, to achieve the maximum percent sequence identity. In yet another embodiment, the percentage is calculated not considering any conservative substitutions as part of the sequence identity. Conservative substitutions are well known in the art. Algorithms that are suitable for determining percent sequence identity and sequence homology are the BLAST and BLAST 2.0 algorithms, which are described in Altschul, et al., *Nuc. Acids Res.*, 25:3389-3402 (1977) and Altschul, et al., *J. Mol. Biol.*, 215:403-410 (1990).

Identity and/or homology may also refer to a sequence that hybridizes to a reference sequence under stringent conditions.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis, et al. (1990) PCR Protocols, A Guide to Methods and Applications, Academic Press, Inc. N.Y.).

However, nucleic acids that do not hybridize to each other under stringent conditions still share relevant identity and/or homology if the polypeptides which they encode are substantially identical, as discussed above.

The siRNA described herein may be full-length oligonucleotides, biologically active fragments, or variants thereof which retain specific biological activity. The biological activity is, in one embodiment, the ability of the siRNA to bind to the target sequence (for example, cnr1/ CNR1 sequence), resulting in suppression of the transcription of the target gene. Variants may comprise analogs wherein one or more of the specified (i.e., naturally encoded) nucleotides is deleted or replaced, or wherein one or more non-specified nucleotides are added: (1) without loss of the above-iterated biological activity. Deletion variants contemplated also include fragments lacking portions of the siRNA not essential for the biological activity, and insertion variants include fusion siRNA, in which the wild-type oligonucleotide or fragment thereof has been fused to another oligonucleotide.

Variant siRNAs include those wherein conservative substitutions have been introduced by modification of polynucleotides. Conservative substitutions are recognized in the art (see, for example, Lehninger, (Biochemistry, Second Edition (1975) W.H. Freeman & Co., pp. 71-77).

Additional modifications of the siRNA described herein include 2'O methyl RNA, biotin, and digoxigenin. The siRNA can also be labeled with fluorescent dye to track its delivery and uptake.

Carrier System

In some embodiments, the siRNA molecule described herein further comprises a carrier system, e.g., to deliver the siRNA molecule into a cell of a mammal Non-limiting examples of carrier systems suitable for use in the present invention include nucleic acid-lipid particles, liposomes, micelles, virosomes, nucleic acid complexes, and mixtures thereof. In certain instances, the siRNA molecule is complexed with a lipid such as a cationic lipid to form a lipoplex. In certain other instances, the siRNA molecule is complexed with a polymer such as a cationic polymer (e.g., polyethylenimine (PEI)) to form a polyplex. The siRNA molecule may also be complexed with cyclodextrin or a polymer thereof. Preferably, the siRNA molecule is encapsulated in a nucleic acid-lipid particle. Most preferably, the siRNA molecule is encapsulated in glucan.

As used herein, "glucan-encapsulated" can refer to a formulation that provides the siRNA with full encapsulation, partial encapsulation, or both. In some embodiments, the nucleic acid is fully encapsulated in the glucan formulation (e.g., to form a nucleic acid-glucan particle).

In one embodiment, Fluorescein (FITC)-labeled glucan shells can be prepared as described by Tesz, et al. (2011 Biochemical Journal 436:351-362). 1-100 nmoles siRNA are incubated with a delivery peptide. For example, Gene Tools, LLC Endo-Porter delivers substances into the cytosol of cells via an endocytosis-mediated process that avoids damaging the plasma membrane of the cell. The resulting solution can then be added to 1-50 mg of FITC-glucan shells and then vortexed and incubated for 1 hour. The siRNA-loaded GeRPs are then resuspended in PBS and sonicated to ensure homogeneity of the GeRP preparation.

The terms "glucan-encapsulated siRNA", "siRNA particles", "GeRPs", and "particles" and the like are used interchangeably herein.

Transfer of an exogenous nucleic acid molecule, e.g., siRNA, into a host cell or organism by a vector, e.g., glucan particle, can be assessed by directly detecting the presence of the nucleic acid in the cell or organism. Such detection can be achieved by several methods well known in the art. For example, the presence of the exogenous nucleic acid molecule can be detected by Southern blot or by a polymerase chain reaction (PCR) technique using primers that specifically amplify nucleotide sequences associated with the nucleic acid molecule.

siRNAs may be detected and quantified herein by any of a number of means well known to those of skill in the art. The detection of nucleic acids proceeds by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

A variety of nucleic acid hybridization formats are known to those skilled in the art. For example, common formats include sandwich assays and competition or displacement assays. Hybridization techniques are generally described in,, e.g., "Nucleic Acid Hybridization, A Practical Approach," Eds. Hames and Higgins, IRL Press (1985). The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known.

An alternative means for determining the level of transcription is in situ hybridization. In situ hybridization assays are well known and are generally described in Angerer, et al., Methods Enzymol., 152:649 (1987).

Transfer of an exogenous nucleic acid molecule, e.g., siRNA, can also be detected by measuring its activity. In one embodiment, siRNA activity can be measured indirectly as a decrease in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non-coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual RNAi's would be assayed by modulation of the reporter gene. Reporter genes useful in the methods of the present invention might include acetohydroxyacid synthase (AHAS), alkaline phosphatase (AP), beta galactosidase (LacZ), beta glucoronidase (GUS), chloramphenicol acetyl-transferase (CAT), green fluorescent protein (GIP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g., fluorescence spectroscopy, Fluorescence Activated Cell Sorting (FACS), fluorescence microscopy) and antibiotic resistance determination.

CB1R Silencing/Knockout

In certain embodiments, the siRNA molecule described herein contacts (interacts with) the targeted mRNA from the gene (e.g., cnr1/CNR1), whereby the expression of the target gene is modulated, and expression is silenced, reduced, or inhibited. To examine the extent of gene silencing, a test sample (e.g., a biological sample from an organism of interest expressing the target gene or a sample of cells in culture expressing the target gene) is contacted with an siRNA that silences, reduces, or inhibits expression of the target gene. Expression of the target gene in the test sample is compared to expression of the target gene in a control sample that is not contacted with the siRNA. Control samples are assigned a value of 100%. Silencing, inhibition, or reduction of expression of a target gene is achieved when the value of test the test sample relative to the control sample is about 95%, 90%, 85%, 80%, 75%, 70%, 65%, 60%, 55%, 50%, 45%, 40%, 35%, 30%, 25%, 20%, or 10%. Suitable assays include, e.g., examination of protein or mRNA levels using techniques known to those of skill in the art such as dot blots, Northern blots, in situ hybridization, ELISA, immunoprecipitation, enzyme function, as well as phenotypic assays known to those of skill in the art.

Reproducible silencing/knockout of the target gene may be seen within four hours of delivery, with maximum down-regulation observed, in certain embodiments, in 24-48 hours. The degree of RNA interference is, in one embodiment, proportional to the level of mature mRNA and translated proteins. Thus, down-regulation can, for example, be quantified via measurement of the target protein activity or, more preferably, via measurement of the target mRNA level (for example, using quantitative PCR).

Interference activity against target nucleic acids ultimately must be established experimentally in cells which express the target nucleic acid. To determine the interference capability of the RNAi sequence, an RNAi-containing vector is transfected into appropriate cell lines which express that target nucleic acid. Each selected RNAi construct is tested for its ability to modulate steady-state mRNA of the target nucleic acid. In addition, any target mRNAs that "survive" the first round of testing are amplified by reverse transcriptase-PCR and sequenced (see, for example, Sambrook, J. et al. "Molecular Cloning: A Laboratory Manual," 2nd addition, Cold Spring Harbor Laboratory Press, Plainview, N.Y. (1989)). These sequences are analyzed to determine individual polymorphisms that allow mRNA to escape the current library of RNAi's. This information is used to further modify RNAi constructs to also target rarer polymorphisms.

Treatment/Therapy

In certain embodiments, the inventive methods treat (e.g., alleviate, ameliorate, relieve, delay onset of, inhibit progression of, reduce severity of, and/or reduce incidence of one or more symptoms or features of) and/or prevent type 2 diabetes mellitus (T2DM).

An individual referred to as "suffering from" a disease, disorder, and/or condition (e.g., type 2 diabetes mellitus (T2DM)) herein has been diagnosed with and/or displays one or more symptoms of the disease, disorder, and/or condition.

As used herein, the term "at risk" for disease (e.g., type 2 diabetes mellitus (T2DM)), refers to a subject (e.g., a human) that is predisposed to contracting the disease and/or expressing one or more symptoms of the disease. Such subjects include those that express certain genetic markers shown to be associated with an increased risk for T2DM, those with familial presence of T2DM, those with impaired glucose tolerance (IGT), those with impaired fasting glycaemia (IFG), those affected by certain environmental or behavioral factors (unhealthy diet, obesity, sedentary lifestyle), those with specific fat distribution (increased in abdomen), those of a certain race, those with pre-diabetes, those with (or having had) gestational diabetes.

The term subject "at risk" includes subjects "suffering from disease," i.e., a subject that is experiencing the disease (e.g., type 2 diabetes mellitus (T2DM)). It is not intended that the present invention be limited to any particular signs or symptoms. Thus, it is intended that the present invention encompasses subjects that are experiencing any range of disease, from sub-clinical infection to full-blown disease, wherein the subject exhibits at least one of the indicia (e.g., signs and symptoms) associated with the disease.

Symptoms of T2DM include, without limitation, increased thirst, frequent urination, increased hunger, weight loss, fatigue, blurred vision, slow-healing sores, frequent infections, and areas of darkened skin (e.g., acanthosis nigricans).

The terms "treat," "treatment," or "treating", as used herein, refer to any method used to partially or completely alleviate, ameliorate, relieve, inhibit, prevent, delay onset of, reduce severity of and/or reduce incidence of one or more symptoms or features of a disease, disorder, and/or condition (e.g., type 2 diabetes mellitus (T2DM)). Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

In some embodiments, methods of treatment involve stratification of a patient population based on prior treatment. Such methods involve steps of determining whether a patient has received treatment. In some embodiments, if it is determined that a patient has previously received or is presently receiving treatment, that patient may receive less concentrated, less potent, and/or less frequent doses of the siRNA composition. If it is determined that a patient has not previously received treatment or is not presently receiving treatment, that patient may receive more concentrated, more potent, and/or more frequent doses of the siRNA compositions.

In one embodiment, the siRNA composition is administered in combination with a distinct therapy. Known treatments of T2DM include, without limitation, oral medicines such as Metformin, short-acting sulfonylurea (for example, glipizide), thiazolidinedione, GLP-agonist, meglitinide, and insulin treatment (injections, DPP-IV inhibitors, α-glucosidase inhibitors).

Treatment goals include, without limitation, blood sugar control (levels to normal or near-normal) and cardiovascular risk control (lower the increased risk of heart disease to normal or near-normal).

A number of factors can be taken into account when determining the distinct therapy, including, for example, the clinical situation of the patient (for example, adult, child, or pregnant female, with either mild or severe T2DM, or at low or great risk of developing T2DM).

Efficacy of treatment can be evaluated by a variety of methods. For example, a decrease in the expression of cnr1/CNR1 would indicate successful interference. Such interference could then be correlated with clinical improvement in diabetic indicators, including (without limitation) reductions in blood glucose and hemoglobin A1c levels, and indicators of improved β-cell function, such as improved glucose-induced insulin release.

Composition

The compositions of the present invention are preferably given to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of who/what is being treated. Prescription of treatment, e.g., final decisions on acceptable dosage etc., can be readily determined by the person of ordinary skill in the art. Thus, an siRNA composition as described herein comprises a protective and/or therapeutic and non-toxic amount of the composition. Suitable dosage amounts can be determined by the person skilled in the art.

In general, a composition as described herein will include a "therapeutic agent" (the CB1R knockdown siRNA), in addition to one or more inactive, agents such as a sterile, biocompatible pharmaceutical carrier including, but not limited to, sterile water, saline, buffered saline, or dextrose solution. Alternatively or additionally, the composition may comprise a pharmaceutically acceptable excipient, which, as used herein, includes any and all solvents, dispersion media, diluents, or other liquid vehicles, dispersion or suspension aids, disintegrating agents, surface active agents, isotonic agents, thickening or emulsifying agents, preservatives, buffering agents, solid binders, granulating agents, lubricants, coloring agents, sweetening agents, flavoring agents, perfuming agents, and the like, as suited to the particular dosage form desired. Remington's The Science and Practice of Pharmacy, 21st Ed., A. R. Gennaro, (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component of the composition, its use is contemplated to be within the scope of this invention.

Thus, the siRNA compositions described herein and for use in accordance with the present invention, may include, in addition to the active ingredient, a pharmaceutically or physiologically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

The compositions described herein may, in another embodiment, be formulated using a diluent. Exemplary "diluents" include water, physiological saline solution, human serum albumin, oils, polyethylene glycols, glycerin, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose. Exemplary "carriers" include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

Compositions as described herein may, in still another embodiment, contain an excipient. The term "excipient" refers herein to any inert substance (e.g., gum arabic, syrup, lanolin, starch, etc.) that forms a vehicle for delivery of a therapeutic agent. The term excipient includes substances that, in the presence of sufficient liquid, impart to a composition the adhesive quality needed for the preparation of pills or tablets.

In further embodiments, interfering agent and/or binding agent polypeptides, nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in the compositions described herein. In some embodiments, interfering agents and/or binding agents that are not polypeptides, e.g., that are small molecules, umbrella topology glycans and mimics thereof, carbohydrates, aptamers, polymers, nucleic acids, etc., are included in the compositions.

The inventive methods described herein can, in certain embodiments, be carried out in vitro or in vivo by first forming the particles (glucan-encapsulated siRNA) as described herein and then contacting the particles with the cells for a period of time sufficient for delivery of the nucleic acid to the cells to occur.

The particles can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

The particles can be administered either alone or in a mixture with a physiologically-acceptable carrier (such as physiological saline or phosphate buffer) selected in accordance with the route of administration and standard pharmaceutical practice. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc.

The pharmaceutical carrier is generally added following particle formation. Thus, after the particle is formed, the particle can be diluted into pharmaceutically acceptable carriers such as normal saline.

The concentration of particles in the pharmaceutical formulations can vary widely, i.e., from less than about 0.05%, usually at or at least about 2-5% to as much as 10 to 30% by weight and will be selected primarily by fluid volumes, viscosities, etc., in accordance with the particular mode of administration selected. For example, the concentration may be increased to lower the fluid load associated with treatment.

The glucan-encapsulated siRNA compositions described herein may be sterilized by conventional, well known sterilization techniques. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

Administration

The mode of administration of an siRNA composition as described herein is any suitable route that delivers a preventive and/or therapeutic amount of the composition to the subject and is described below. However, the composition is generally administered orally or parenterally.

Systemic delivery for in vivo therapy, i.e., delivery of a therapeutic nucleic acid to a distal target cell via body systems such as the circulation, has been achieved using nucleic acid-lipid particles such as those disclosed in PCT Publication No. WO 96/40964 and U.S. Pat. Nos. 5,705,385; 5,976,567; 5,981,501; and 6,410,328. This latter format provides a fully encapsulated nucleic acid-lipid particle that protects the nucleic acid from nuclease degradation in serum, is nonimmunogenic, is small in size, and is suitable for repeat dosing.

Thus, in vivo administration routes include oral (PO), intravenous (IV), intraperitoneal (IP), intragastric (IG), and/or through a portal vein catheter.

For oral administration, the composition may be presented as capsules, tablets, dissolvable membranes, powders, granules, or as a suspension. The composition may have conventional additives, such as lactose, mannitol, corn starch, or potato starch. The composition also may be presented with binders, such as crystalline cellulose, cellulose derivatives, acacia, corn starch, or gelatins. Additionally, the composition may be presented with disintegrators, such as corn starch, potato starch, or sodium carboxymethylcellulose. The composition may be further presented with dibasic calcium phosphate anhydrous or sodium starch glycolate. Finally, the composition may be presented with lubricants, such as talc or magnesium stearate.

For parenteral administration, the composition may be prepared with a sterile aqueous solution, which is preferably isotonic with the blood of the subject. Such a composition may be prepared by dissolving a solid active ingredient in water containing physiologically compatible substances, such as sodium chloride, glycine, and the like, and having a buffered pH compatible with physiological conditions, so as to produce an aqueous solution, then rendering the solution sterile. The composition may be presented in unit or multi-dose containers, such as sealed ampoules or vials. The composition also may be delivered by any mode of injection, including any of those described herein.

Solid dosage forms for oral administration include capsules, tablets, pills, powders, dissolvable membranes, and granules. In such solid dosage forms, the glucan-encapsulated siRNA is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), taste/olfactory components, and mixtures thereof. In the case of capsules, tablets and pills, the dosage form may comprise buffering agents.

Compositions also may be released or delivered from an osmotic mini-pump or other timed-release device. The release rate from an elementary osmotic mini-pump may be modulated with a microporous, fast-response gel disposed in the release orifice. An osmotic mini-pump would be useful for controlling release, or targeting delivery, of the composition.

Compositions may be administered or introduced to a subject by known techniques used for the introduction of drugs, including, for example, injection and transfusion. In some embodiments, it may be desirable to introduce the composition directly to a specific area by injection or by some other means (e.g., by introducing the composition into the blood or another body fluid).

In one or more embodiments, the compositions of the present invention may employ various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

The composition as described herein may be administered to a subject, either alone or in combination with one or more drugs used to treat the T2DM or a symptom of the same. The composition may be administered alone or in combination with other treatments, either simultaneously or sequentially, dependent upon the condition to be treated.

Glucan-encapsulated siRNA (particles) can be detected using any methods known in the art. For example, a label can be coupled directly or indirectly to a component of the particle using methods well known in the art. A wide variety of labels can be used, with the choice of label depending on sensitivity required, ease of conjugation with the particle component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CYDYES™, and the like; radiolabels such as $^3$H, $^{125}$I, $^{35}$S, $^{14}$C, $^{32}$P, $^{33}$P etc.; enzymes such as horse radish peroxidase, alkaline phosphatase, etc.; spectral colorimetric labels such as colloidal gold or colored glass or plastic beads such as polystyrene, polypropylene, latex, etc. The label can be detected using any means known in the art.

Dosages

A composition as described herein may be administered using any amount effective for treatment and/or prevention. The exact amount required will vary from subject to subject, depending on the species, age, and general condition of the subject, the severity of the disease, the particular composition, its mode of administration, its mode of activity, and the like. Compositions are typically formulated in dosage unit form for ease of administration and uniformity of dosage. It will be understood, however, that the total usage of the composition will be decided by the attending physician within the scope of sound medical judgment. The specific therapeutically effective dose level for any particular subject or organism will depend upon a variety of factors including the severity of the disease; the activity of the specific composition employed; the half-life of the composition after administration; the age, body weight, general health, sex, and diet of the subject; the time of administration, route of administration, and rate of excretion of the specific components employed; the duration of the treatment; drugs used in combination or coincidental with the specific components employed; and like factors, well known in the medical arts.

The dosage of the composition can be determined by, for example, first identifying doses effective to elicit a prophylactic and/or therapeutic response. The dosages can be determined from animal studies. For example, the animals can be dosed with a composition candidate, e.g., a composition as described herein, to partially characterize the response induced. In addition, routine human clinical studies can be performed to determine the effective dose for humans.

In one embodiment, a composition dose consists of a range of about 0.2 to about 2 mg/kg GeRPs containing about 10 to about 50 ng/kg siRNA directed against the human CB1R gene (CNR1).

Effective doses may be extrapolated from dose-response curves derived from in vitro and/or in vivo animal models. A therapeutically effective amount, based upon human studies, would, in one embodiment, be sufficient to significantly decrease the expression of CB1R. For some compositions (in certain embodiments), this effective level would result in at least about a 50% decrease, at least about a 60% decrease, at least about a 70% decrease, at least about an 80% decrease, at least about a 90% decrease, or at least about a 95% decrease in expression in comparison to control. For other compositions, a prophylactically effective amount would be one that protects against development of T2DM.

In one embodiment, the composition may be administered to a subject at risk of developing T2DM, in an amount effective to prevent the disorder in the subject. As used herein, the phrase "effective to prevent the disorder" includes effective to hinder or prevent the development or manifestation of clinical impairment or symptoms resulting from the disorder, or to reduce in intensity, severity, and/or frequency, and/or delay of onset of one or more symptoms of the disorder.

Combinations

As mentioned above, compositions as described herein can be administered to a subject either alone or in combination with one or more other therapeutic agents. By "in combination with," it is not intended to imply that the agents must be administered at the same time or formulated for delivery together, although these methods of delivery are within the scope of the invention. Compositions as described herein can be administered concurrently with, prior to, or subsequent to, one or more other desired therapeutics or medical procedures. It will be appreciated that therapeutically active agents utilized in combination may be administered together in a single composition or administered separately in different compositions. In general, each agent will be administered at a dose and/or on a time schedule determined for that agent.

In general, each agent (in this context, one of the "agents" is the glucan-encapsulated siRNA) will be administered at a dose and on a time schedule determined for that agent. Additionally, the invention encompasses the delivery of the compositions in combination with agents that may improve their bioavailability, reduce or modify their metabolism, inhibit their excretion, or modify their distribution within the body. Although the compositions can be used for treatment and/or prophylaxis of any subject, they are preferably used in the treatment and/or prophylaxis of humans.

The particular combination of therapies (e.g., therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an agent useful for treating, preventing, and/or delaying the onset of T2DM may be administered concurrently with another agent useful for treating, preventing, and/or delaying the onset of T2DM), or they may achieve different effects (e.g., prevention of severe illness or control of adverse effects or symptoms of T2DM).

In general, it is expected that agents utilized in combination will be utilized at levels that do not exceed the levels at which they are utilized individually. In some embodiments, the levels utilized in combination will be lower than those utilized individually.

Kits

Kits comprising glucan-encapsulated siRNA are provided in an additional embodiment. Kits can include one or more other elements including, but not limited to, instructions for use; other reagents, e.g., a diluent, devices or other materials for preparing the composition for administration; pharmaceutically acceptable carriers; and devices or other materials for administration to a subject. Instructions for use can include instructions for therapeutic application including suggested dosages and/or modes of administration, e.g., in a human subject, as described herein.

In another embodiment, a kit according to the invention may comprise a container which is compartmentalized for holding the various elements of the glucan-encapsulated siRNA (e.g., the nucleic acids and the individual lipid components of the glucan particles). In some embodiments, the kit may further comprise an endosomal membrane destabilizer (e.g., calcium ions). The kit typically contains the glucan-encapsulated siRNA compositions of the present invention, preferably in dehydrated form, with instructions for their rehydration and administration. In certain instances, the particles and/or compositions comprising the particles may have a targeting moiety attached to the surface of the particle. Methods of attaching targeting moieties (e.g., antibodies, proteins) to lipids (such as those used in the present particles) are known to those of skill in the art.

In another embodiment, a kit according to the invention can further contain at least one additional reagent, such as a diagnostic or therapeutic agent, e.g., a diagnostic agent to monitor a response to the composition in the subject, or an additional therapeutic agent as described herein.

EXAMPLES

The following examples are provided for illustrative purposes only and are not intended to limit the scope of the invention.

Example 1. Peripheral $CB_1R$ Blockade Delays the Progression of Diabetes of ZDF Rats Zucker diabetic fatty (ZDF) rats were used to assess the role of endocannabinoids and $CB_1R$ in glycemic control and β-cell loss Animal protocols were approved by the Institutional Animal Care and Use Committee of the NIAAA, NIH. Male ZDF rats with their lean controls were obtained from Charles River Laboratories (Wilmington, Mass. 01887, USA). Rats were individually housed and maintained under a 12-h light/dark cycle and fed ad libitum with a standard laboratory diet (STD, NIH-31 rodent diet).

ZDF rats received JD5037 or vehicle (4% DMSO+1% Tween 80 in PBS) by oral gavage according to 2 different protocols. JD5037 was synthesized and its pharmacological properties analyzed as described earlier (Tam, et al. 2012 Cell Metab 16, 167-179). In brief, the accession number for the Cannabinoid receptor 1 was located, which is NM_012784. At the Dharmacon website (Thermo-Scientific): thermoscientificbio.com/design-center/?Parent=17179869885, the accession number was entered, and the desired region for SiRNA design was selected (in this case, the ORF); then 'blast' was selected with option for Rat (rattus Norvegicus). Candidates were selected from among the ones with the highest scores and a GC content between 30 and 40% for testing. Of note, this protocol should provide ample guidance for identifying human siRNA sequences and CNR1 regions of interest. To achieve acceptable purity, a purification grade A4 was indicated.

Of the four sequences;

```
siRNA A:
sense sequence
                                            (SEQ ID NO: 5)
GAUGUGGACUAUCGCAAUAUU, antisense sequence
                                            (SEQ ID NO: 6)
UAUUGCGAUAGUCCACAUCUU;

siRNA B:
sense sequence
                                            (SEQ ID NO: 7)
GCCUAUAAGAGGAUCGUCAUU,
```

```
antisense sequence
                                            (SEQ ID NO: 8)
UGACGAUCCUCUUAUAGGCUU;

siRNA C:
sense sequence
                                            (SEQ ID NO: 9)
GCAUCAAGAGCACCGUUAAUU, antisense sequence
                                            (SEQ ID NO: 10)
UUAACGGUGCUCUUGAUGCUU;
and siRNA D:
sense sequence
                                            (SEQ ID NO: 11)
CCGUUAAGAUCGCGAAGGUUU, antisense sequence:
                                            (SEQ ID NO: 12)
ACCUUCGCGAUCUUAACGGUU,
``` the sequence of the siRNA producing the greatest degree of knockdown was siRNA C.

The specificity of each siRNA was measured in terms of knockdown of CB2 receptor expression, and a dose-response analysis of siRNA C was carried out.

In the first one, 8-week old diabetic ZDF rats were given 3 mg/kg JD5037 or vehicle for 28 days with lean controls receiving vehicle only. In the second protocol, similar treatment was started in 6-week old pre-diabetic ZDF rats and age-matched lean controls, and treatment continued for 12 weeks until the age of 18 weeks. Body weight and food intake were monitored daily. At the end of treatment in both protocols, rats were sacrificed by decapitation, the brain, liver, kidney, pancreas and combined fat pads were removed, weighed, and snap-frozen in liquid nitrogen or fixed in formalin, and trunk blood was collected for determining endocrine and biochemical parameters. Adiposity index was defined as the combined weight of the epidydimal, retroperitoneal and inguinal fat pads, expressed as % of total body weight. In the second protocol, blood samples were taken weekly to assess the progression of T2DM by measuring blood glucose and monthly to measure insulin and c-peptide levels.

Blood Chemistry

Blood glucose levels were determined using the Elite glucometer (Bayer, Pittsburgh, Pa.). Serum alanine aminotransferase (ALT), total cholesterol, triglycerides. Plasma insulin was measured using the Ultra Sensitive rat Insulin ELISA kit (Crystal Chem Inc). Hemoglobin A1c was determined using the Rat Hemoglobin A1c (HbA1c) assay kit (Crystal Chem) and c-peptide was quantified by ELISA (C-peptide (rat) ELISA, ALPCO). Serum leptin and adiponectin were determined by ELISA (B-Bridge International). α-amylase, lipase, and uric acid concentrations were determined using commercially available colorimetric kits (BioAssay Systems). TNF-α and IL-1β were determined using TNF-α ELISA Kit (for Lysates) (RayBiotech, Inc.) and IL1β Rat ELISA Kit (Abeam), respectively.

Liver Parameters

To determine intra-hepatic triglyceride and cholesterol content, liver tissue was extracted as described previously (Folch, et al. 1957 J Biol Chem 226:497-509). After extraction, 0.5 ml of organic phase was transferred to a clean tube containing 1 ml of 2% Triton X-100 in chloroform and dried using nitrogen. The residue was re-solubilized in 1 ml of distilled water and used for triglycerides content using EnzyChrom™ Triglyceride Assay Kit.

Thus, eight-week-old male, diabetic ZDF rats were treated orally with the non-brain-penetrant $CB_1R$ inverse agonist JD5037 or vehicle for 28 days. Relative to lean controls, vehicle-treated ZDF rats were obese and hyperphagic (FIG. 1a), had increased hepatic triglyceride content, increased hepatic expression of the lipogenic enzymes fatty acid synthase and stearoyl CoA desaturase-1 (FIG. 1b), and had overt diabetes, indicated by pronounced hyperglycemia, elevated HbA1c levels and moderate hyperinsulinemia (FIG. 1c). Furthermore, they had extremely elevated plasma triglyceride and cholesterol levels (Table 1, below, showing the effects of peripheral $CB_1R$ antagonism on plasma levels of hormonal/metabolic variables).

TABLE 1

|  |  | Lean | ZDF + Veh | ZDF + JD5037 | ZDF + Clodronate |
| --- | --- | --- | --- | --- | --- |
| Leptin | ng/mL | 3.46 ± 0.15 | 12.91 ± 0.48*** | 9.48 ± 0.31***,### | 11.97 ± 0.98*** |
| Adiponectin | µg/mL | 4.60 ± 0.29 | 2.44 ± 0.18*** | 5.70 ± 0.07**,### | 2.35 ± 0.23*** |
| TG | mg/dL | 63.2 ± 10.14 | 1196 ± 106.67*** | 817.6 ± 31.36***,### | 1136 ± 114*** |
| Cholesterol | mg/dL | 88 ± 7.35 | 164.8 ± 3.85*** | 104.8 ± 3.85### | 159 ± 17*** |
| Uric acid | µg/mL | 2.27 ± 0.13 | 4.84 ± 0.36*** | 2.57 ± 0.04### | 5.01 ± 0.44*** |
| IL-1β | ng/mL | 4.06 ± 0.41 | 14.05 ± 0.88*** | 7.63 ± 0.78 **,### | 8.42 ± 0.45 **,### |
| TNF-α | pg/mL | 1.71 ± 0.25 | 3.50 ± 0.74*** | 0.83 ± 0.07**,### |  |

ZDF rats were treated daily for 28 days with vehicle or 3 mg/kg/day of JD5037. Figures in the Table 1 represent means ± SEM from 20 animals/group,
*P < 0.05,
**P < 0.01,
***P < 0.001 Lean vs. others groups.
P < 0.05,
P < 0.01,
P < 0.001 ZDF + Veh vs. ZDF + JD5037.
†P < 0.05,
††P < 0.01,
†††P < 0.001 ZDF + Veh vs. ZDF + Clodronate.

Figure 2:
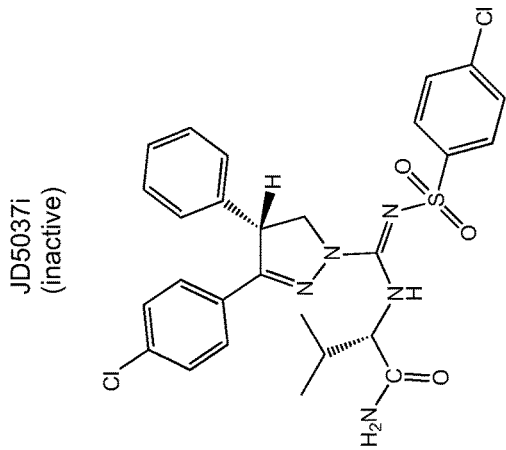
FIG. 2a describes the structure of JD5037 and its inactive diastereomer.
FIG. 2b shows, in bar graph form, the $CB_1R$ specificity of the effects of JD5037 in reversing hyperglycemia and increasing insulin and c-peptide levels in ZDF rats. Vehicle-treated lean (open columns), ZDF rats (gray columns), JD5037-treated ZDF rats (black columns), and JD5037i-treated rats (open columns with arrows) were sacrificed after 1 week of treatment; blood glucose, insulin, and c-peptide concentrations were determined as described in the Examples, below. Columns and bars represent means±SEM from 10 animals/group; *P<0.05,  P<0.01, *P<0.001. Note that only JD5037, and not its inactive diastereomer JD5037i, was effective in improving glycemic control in ZDF rats.
Figure 2:
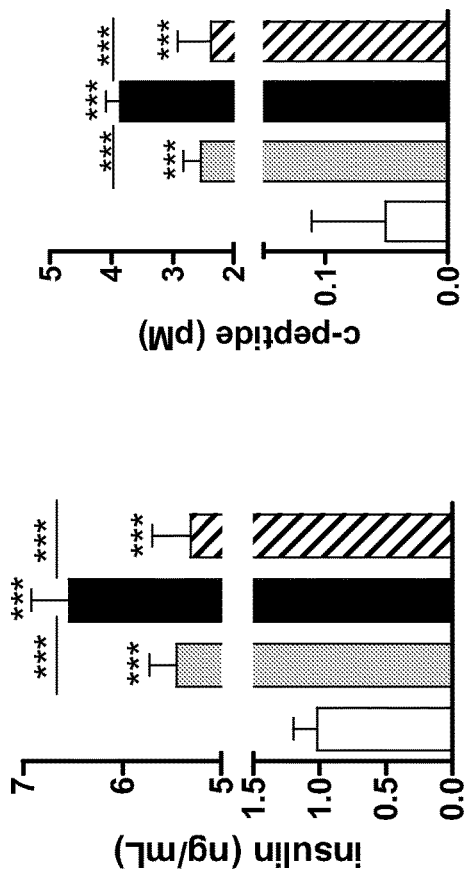
Figure 2:
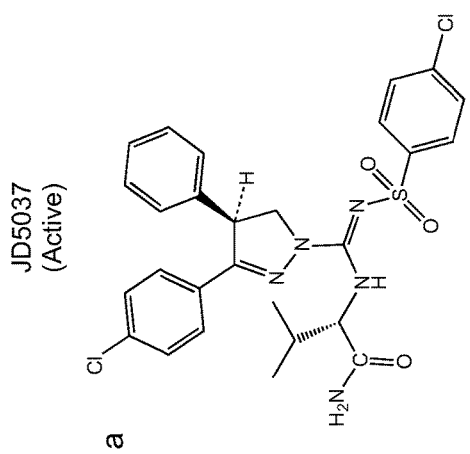
Figure 2:
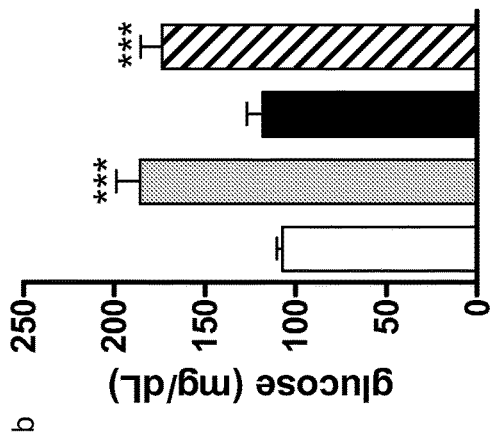

Chronic JD5037 treatment did not affect body weight or adiposity and caused a small reduction in food intake (FIG. 1a), whereas the steatosis, the associated hepatocellular damage, and the increased lipogenic gene expression were greatly attenuated (FIG. 1b). JD5037 treatment completely reversed the hyperglycemia of ZDF rats, and their modest hyperinsulinemia was paradoxically enhanced along with increased C-peptide levels (FIG. 1c), suggesting improved β-cell function and survival. Unlike JD5037, its inactive diastereomer did not affect plasma glucose, insulin and c-peptide levels (FIG. 2). Normoglycemia coupled with hyperinsulinemia in JD5037-treated rats suggest continued insulin resistance. Indeed, the insulin resistance of ZDF rats, which was primarily due to decreased peripheral glucose uptake, was not significantly affected by JD5037, as indicated by euglycemic-hyperinsulinemic clamp experiments (FIG. 1d).

Hyperinsulinemic Euglycemic Clamp

Clamps and glucose tracer analyses in conscious, cannulated rats were performed as described: right jugular vein of 3 rats per group was catheterized a week prior to the experiment, and clamps were performed by continuous infusion of insulin at 3 mU/kg/min and co-infusion of 3H-D-glucose to maintain euglycemia. The protocol for radioactive clamps to evaluate glucose fluxes was adapted from Buettner, et al. (Buettner, et al. 2005 *J Clin Invest* 115:1306-1313). 3H-D-glucose (Perkin Elmer) was first infused at 0.8 µCi/min for one minute and then at 0.04 µCi/min for 2 h prior to insulin infusion, and the tritiated glucose infusion was pursued during the rest of the experiment at the same rate. 10 µl of blood were sampled from the tail 15 and 5 min before starting insulin infusion and 30, 20, 10 minutes before the end of the experiment.

Blood samples were centrifuged in order to obtain serum. Serum was snap frozen on dry ice and, once all the samples were available, 5 µl serum was transferred to 25 µl dionized water and then mixed with 25 µl of 0.1N $ZnSO_4$. Samples were precipitated with addition of 25 µl of 0.1N $Ba(OH)_2$. After centrifugation, the supernatant was dried overnight, resuspended in water, and counted in scintillation liquid.

Glucose turnover was calculated as the ratio of tritiated glucose infusion rate over the specific activity of blood glucose.

Figure 3:
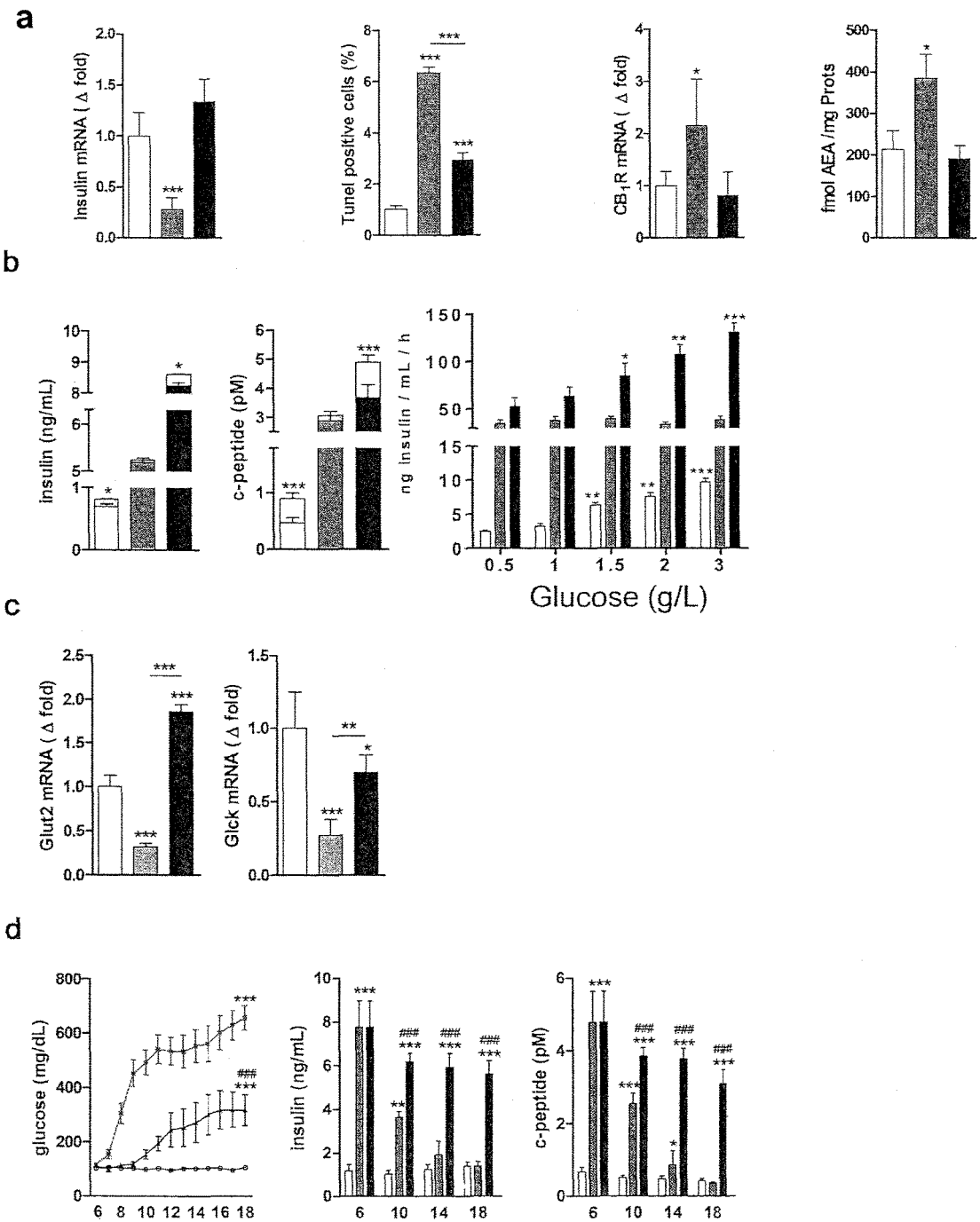
FIG. 3 shows that JD5037 treatment prevents and delays the onset of diabetes and β-cell loss in ZDF rats. Treatments, as described for FIG. 1, were started in 8-week-old diabetic (for FIGS. 3a-3c) or 6-week-old prediabetic ZDF rats (for FIG. 3d).
Figure 4:
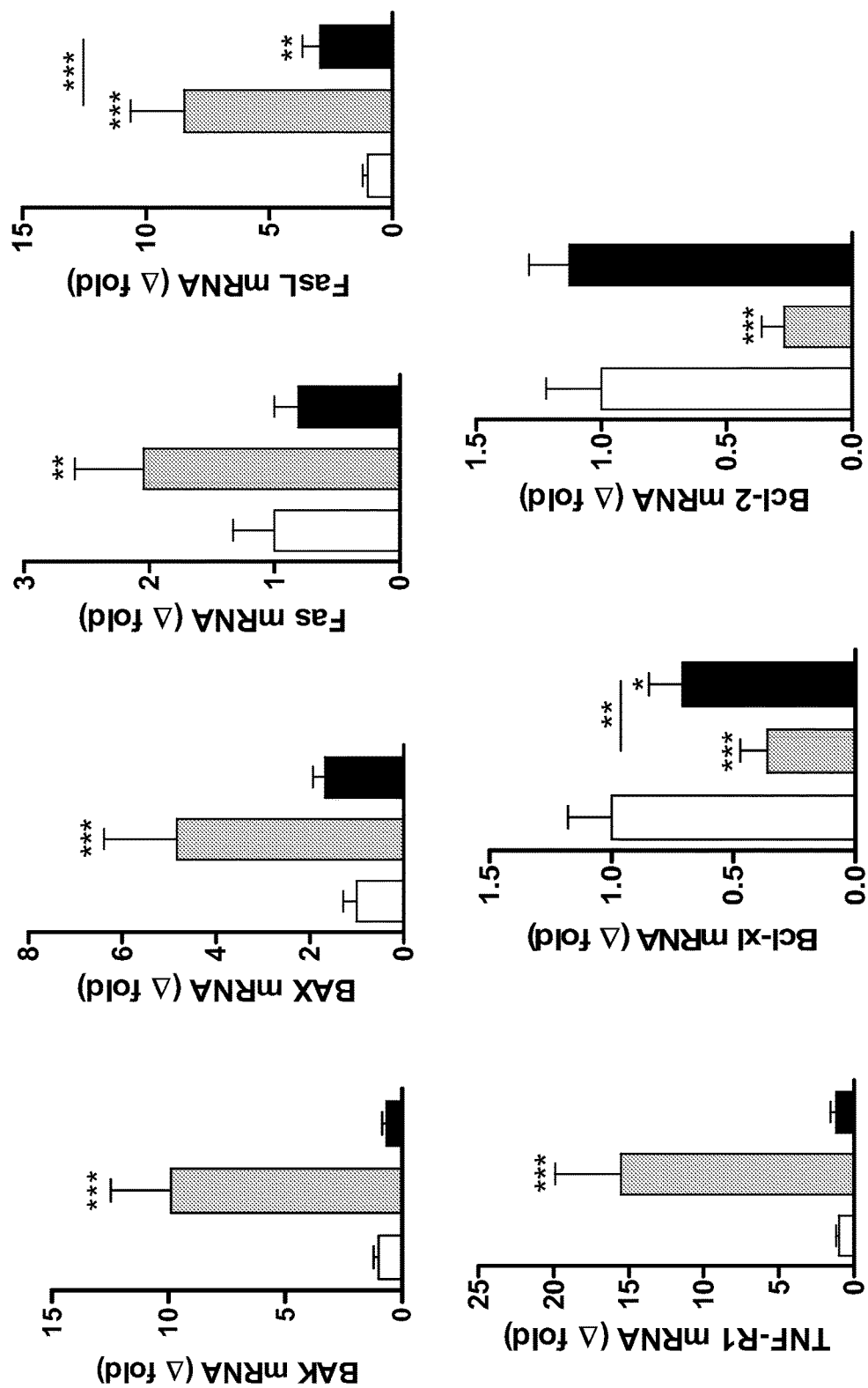
FIG. 4 illustrates, in bar graph form, the effects of $CB_1R$ antagonism on pro- and anti-apoptotic genes in ZDF pancreas. Peripheral $CB_1R$ antagonism reverses the increased expression of pro-apoptotic markers and decreases expression of anti-apoptotic markers in ZDF pancreas. Vehicle-treated lean (open columns) and ZDF rats (gray columns) and JD5037-treated ZDF rats (black columns) were sacrificed after 4 weeks of treatment; their pancreas was removed and analyzed for gene expression as described in the Examples, below. Columns and bars represent means±SEM from 10 animals/group; *P<0.05,  P<0.01, *P<0.001.

JD5037 treatment also normalized insulin mRNA and protein in ZDF islets, probably by preventing β-cell apoptosis. This is indicated by the reduced number of Tunel-positive islet cells (FIG. 3a), the increased expression of the apoptotic markers Bak, Bax, Fas, Fas ligand and TNF-R1 (FIG. 4), and a decrease in the anti-apoptotic markers Bcl-2 and Bcl-xl (FIG. 4). A parallel rise in the expression of $CB_1R$ in islets of ZDF vs. lean rats was reversed by JD5037 (FIG. 3a). Similarly, increased pancreatic anandamide levels were normalized following JD5037 treatment (FIG. 3a). Extraction and measurement of anandamide by LC/MS/MS was performed as described previously (Mukhopadhyay, et al. 2011 *Proc Natl Acad Sci USA* 108:6323-6328).

Pancreas Immunohistology

Pancreas was fixed in 10% neutral buffered formalin (NBF), embedded in paraffin and sectioned (4 nm) onto glass slides. Antibodies used for immunostaining are listed in Table 2. Each bound antibody was revealed using the appropriate ABC-elite-HRP (horseradish peroxidase)/diaminobenzediene (DAB) system (Vector Labs)). To determine if any co-localization was occurring, we used the same couples of antibodies listed in Table 2, below. For detection, secondary Ab coupled to FITC or PE were used (Table 2). Images were viewed with a Fluoview FV10i confocal microscope system (Olympus). Images were then analyzed using image J software and the presence or absence of co-localization was assessed by calculating the Pearson's coefficient.

TABLE 2

| Protein | reference | Specificity | Supplier | dilution |
|---|---|---|---|---|
| Primary Antibodies | | | | |
| Insulin | A0564 | Guinea Pig anti-human | Dako | 1/100 |
| $CB_1R$ | PA1-743 | Rabbit anti-human/rat | Thermo scientific Lifespan Biosciences | 1/200 |
| NLRP3 | LS-B1766 | Goat anti-human | | 1/200 |
| CD68 | ab31630 | Mouse anti-rat/mouse | Abcam | 1/100 |
| CD3 | ab5690 | Rabbit anti-human/rat/mouse | Abcam | 1/200 |
| Secondary Antibodies | | | | |
| | ab6904 | Goat anti-Guinea Pig (FITC) | Abcam | 1/200 |
| | ab7007 | Donkey anti-Rabbit (PE) | Abcam | 1/200 |
| | ab8517 | Rabbit anti-Mouse (FITC) | Abcam | 1/100 |
| | ab7004 | Donkey anti-Goat (PE) | Abcam | 1/100 |

Tunel staining was performed using the TUNEL Apoptosis Detection Kit (GenScript USA Inc). Sections were then counterstained with hematoxylin, Gills Formula (Vector Labs) and analyzed using an Olympus BX41 microscope.

The loss of insulin-producing β-cells in ZDF rats was paralleled by the absence of glucose-stimulated insulin secretion (GSIS), as assessed in vivo by measuring plasma insulin and c-peptide within 5 min of a glucose load and in vitro in isolated, perfused islets.

Isolation of Pancreatic Islets and Measurement of Insulin Secretion

Rats were fasted for 12 h, and tail blood was collected to determine basal insulin and c-peptide levels. Rats were then given glucose (3 g/kg) orally by gavage, and, 5 minutes later, tail blood was again collected for determining insulin and c-peptide levels, with the difference over baseline insulin considered as a measure of glucose-induced insulin release, and the comparison with parallel changes in c-peptide levels used to assess the role of insulin production vs. clearance in the observed change in plasma insulin levels.

After 4 days recovery, pancreata from treated animals were inflated via the common bile duct with a solution of LIBERASE™ TL Research Grade (1.18 U/ml, Roche Diagnostics) and digested for 30 min at 37° C. Islets were purified on a discontinuous Ficoll gradient (GE HEALTHCARE) and hand-picked under a stereomicroscope for immediate assessment of β cell function by static incubation. Right after isolation, batches of 4 islets were pre-incubated for 2 h in RPMI 1640 containing NaHCO3 (2 g/l), HEPES (25 mM), 10% (v/v) neonatal calf serum (Invitrogen), pH 7.2, and 0.5 g/L glucose at 37° C. in an incubator containing 5% $CO_2$. This was followed by successive 1 h incubations in the presence of 0.5, 1, 1.5, 2, and 3 g/L glucose. Supernatants were collected in each step for insulin quantification (Crystal Chem Inc). For each condition, the experiments were performed in triplicate of 5 islets from 5 biological replicates.

JD5037 treatment did not affect elevated basal insulin levels, but restored GSIS (glucose-stimulated insulin secretion) both in vivo and in vitro (FIG. 3b). In parallel, JD5037 normalized the reduced pancreatic expression of glucokinase (Glck) as well as Glut2 (FIG. 3c), which mediates glucose uptake by β-cells.

When pre-diabetic 6-week-old ZDF rats were treated daily with JD5037 for 3 months, their hyperglycemia was attenuated and its development delayed, and the rapid decline in plasma insulin and c-peptide was largely prevented (FIG. 3d). Thus, peripheral $CB_1R$ blockade delays the progression of T2DM and the loss of β-cell function.

Figure 5:
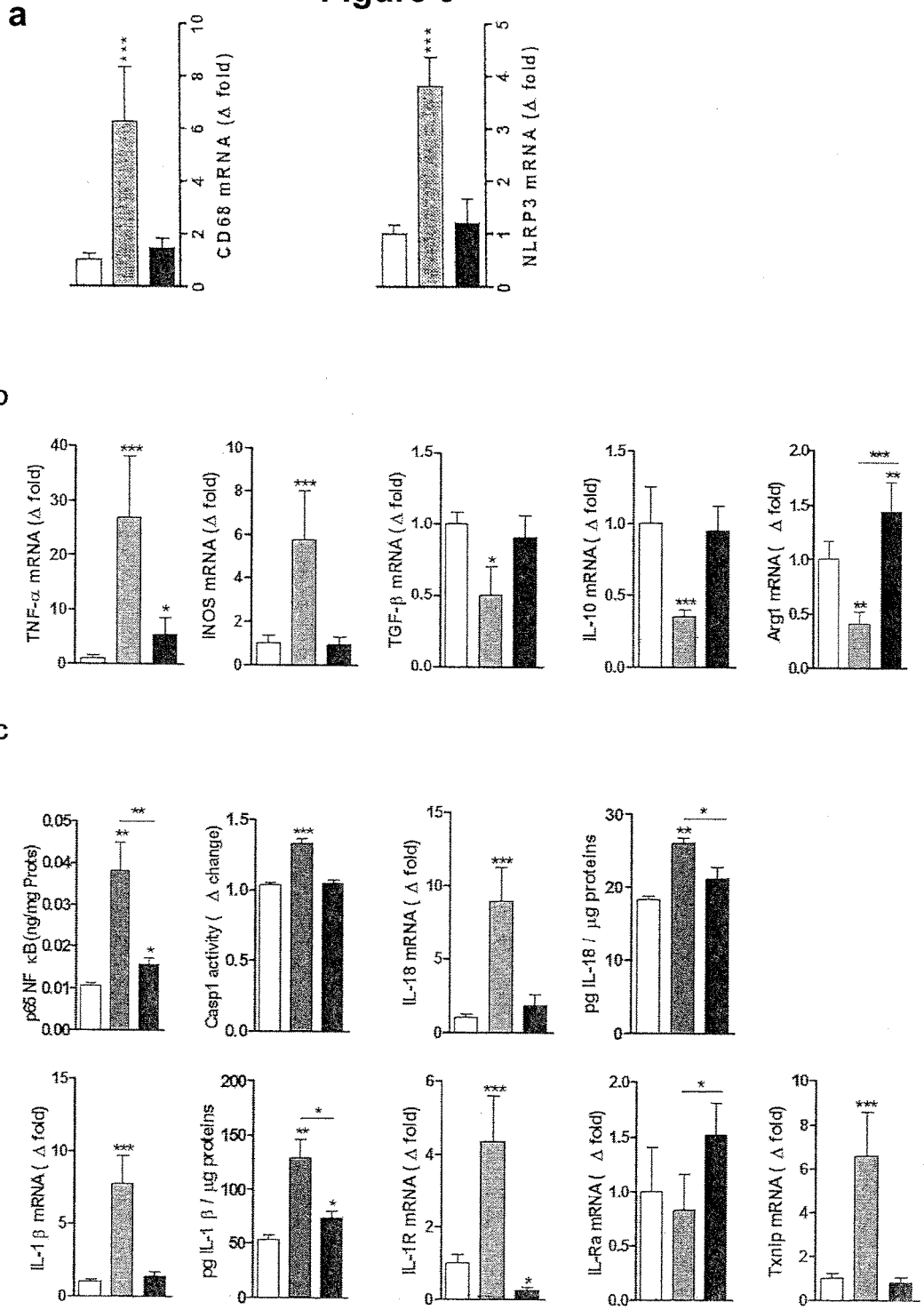
FIG. 5 shows that infiltration of diabetic islets by inflammatory cells and the associated inflammasome activation are reversed by $CB_1R$ blockade.

Example 2. Peripheral $CB_1R$ Blockade Reverses Immune Cell Infiltration and Nlrp3-Mediated Insulitis in ZDF Rats ZDF islets were enlarged with robust infiltration by CD68+ macrophages (FIG. 5a) of the M1 phenotype, as indicated by increased TNFα and iNOS and decreased TGFβ, IL-10 and arginase-1 expression relative to lean controls. JD5037 treatment reduced macrophage infiltration and caused an M1/M2 shift (FIG. 5b). ZDF islets displayed elevated mRNA and protein levels of Nlrp3, IL-1β and IL-18, increased p65 NFκB protein and increased caspase-1 activity (FIG. 5a). The mRNA for thioredoxin-interacting protein TXNIP and the IL-1 receptor were also increased. All these changes were completely reversed by JD5037 treatment, whereas the expression of the IL-1R antagonist was increased (FIG. 5c).

Figure 6:
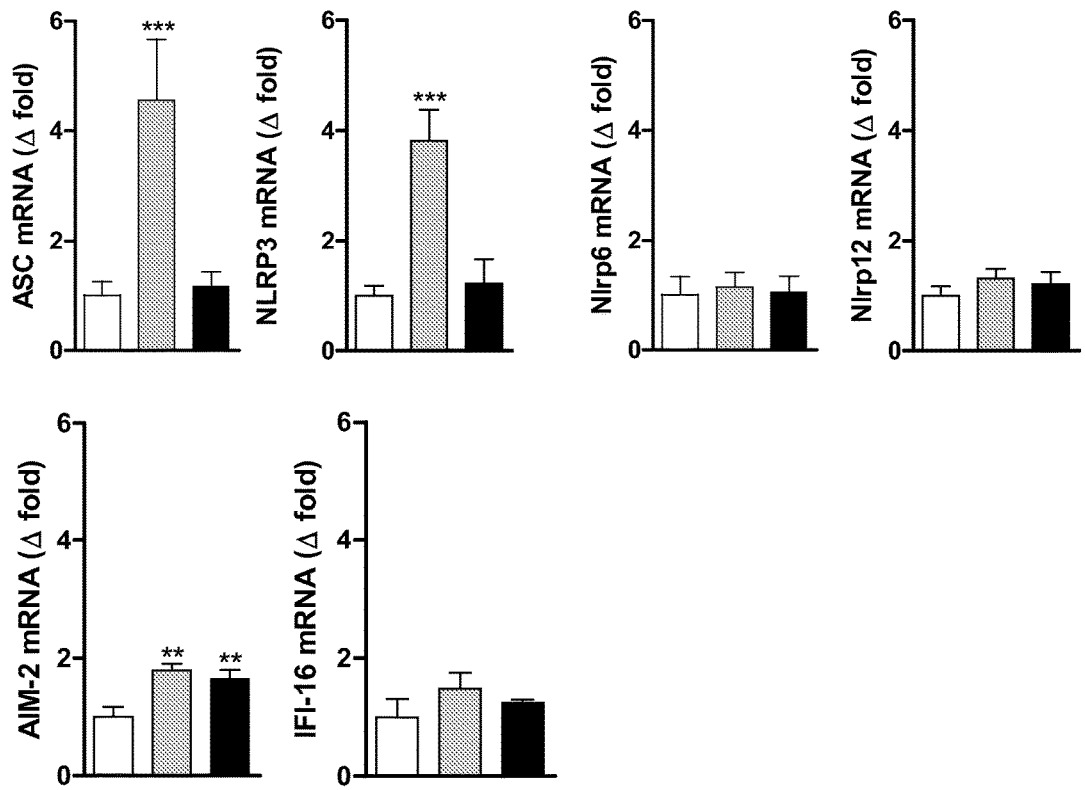
FIG. 6 shows, in bar graph form, that inflammasome activation in the diabetic pancreas is specific for the Nlrp3/ASC inflammasome. Vehicle-treated lean (open columns) and ZDF rats (gray columns) or JD5037-treated ZDF rats (black columns) were analyzed after 4 weeks of treatment as described in the Examples, below. Columns and bars represent means±SEM from 10 animals/group; *P<0.05,  P<0.01, *P<0.001.

The assembly of the functional inflammasome involves the interaction of the pyrin domains of Nlrp3 and the adaptor protein ASC. ASC mRNA was greatly increased in ZDF rats and normalized by JD5037 treatment, whereas the expression of other inflammasome proteins, such as Nlrp6, Nlrp12 and IFI-16, was unaffected, and a small increase in AIM-2 expression was unaffected by JD5037 treatment (FIG. 6). Both $CB_1R$ and Nlrp3 highly significantly co-expressed with CD68 (72.3±5.9% and 84.9±9.8% co-localization, respectively) whereas tissue distribution of $CB_1R$ and insulin did not significantly overlap (5.4±3.7% co-localization). This indicates that $CB_1R$ and Nlrp3 are expressed predominantly by M1 macrophages rather than β-cells in diabetic islets.

Figure 7:
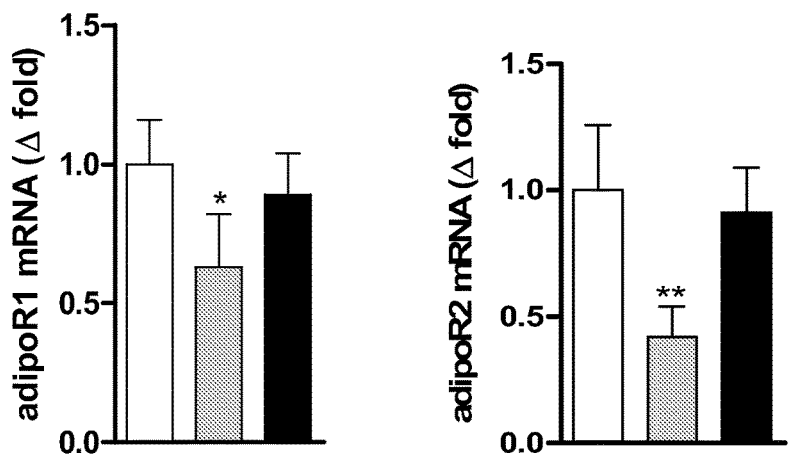
FIG. 7 illustrates, in bar graph form, the effects of peripheral $CB_1R$ antagonism adipoR1 and adipoR2 mRNA expression in the ZDF pancreas. Peripheral $CB_1R$ antagonism reverses the decreased expression of adipoR1 and adipoR2 in the ZDF pancreas. Vehicle-treated lean (open columns) and ZDF rats (gray columns) and JD5037-treated ZDF rats (black columns) were sacrificed after 4 weeks of treatment, and their pancreas was removed and processed for analyses of gene expression as described in the Examples, below. Columns and bars represent means±SEM from 10 animals/group; *P<0.05,  P<0.01, *P<0.001.

The anti-inflammatory function of adiponectin is well recognized, and its effects are mediated by adipoR1 and adipoR2 receptors, both of which are abundantly expressed in islet β-cells. Plasma levels of adiponectin (Table 1, above) as well as the pancreatic expression of its 2 receptors were decreased in ZDF rats, and these changes were reversed by JD5037 treatment (FIG. 7). Plasma levels of uric acid, which has been implicated in proinflammatory changes and decreased adiponectin production, and also in the activation of the Nlrp3 inflammasome, increased in ZDF compared to lean rats in a JD5037-reversible manner (Table 1, above).

Example 3. Macrophage Depletion Protects β-Cells and Delays the Development of Diabetes Macrophages were depleted in 8-week-old ZDF rats by treatment with clodronate-containing liposomes.

Depletion of Pancreatic Macrophages with Clodronate-Containing Liposomes

Clodronate-containing liposomes were prepared as described (Ju, et al. 2001 Chem Res Toxicol 14:1209-1217). Briefly, phosphatidylcholine (86 mg) and 8 mg cholesterol were dissolved in 10 mL of chloroform in a 500 mL round-bottom flask. Chloroform was removed by low vacuum rotary evaporation at 37° C. The thin film that formed on the walls of the flask was dispersed by gentle shaking for 10 min in 10 mL of PBS or 0.6 M clodronate dissolved in PBS. The suspensions were kept under argon for 2 h at room temperature, sonicated for 3 min in a water bath sonicator, and kept under argon for another 2 h. The non-encapsulated clodronate was removed by centrifugation (10,000 g for 15 min) of the liposomes. The white band at the top of the suspension, which contained clodronate-containing liposomes, was retrieved and washed twice with PBS (sterilized) by centrifugation (25,000 g for 30 min) Finally, the pellet was resuspended in 4 mL of sterilized PBS and stored at 4° C. for up to one month before use. Rats were injected i.p. (intraperitoneally) with clodronate-containing liposomes (1 mL) 3 times with a 3-day interval between two consecutive injections. Glycemia was followed every 4 days as previously described. Twenty days after the first injection, animals were sacrificed and tissues were collected. The pancreas was fixed in 10% neutral buffered formalin (NBF), embedded in paraffin and sectioned (4 μm) onto glass slides. Specific staining was performed as described below.

Figure 8:
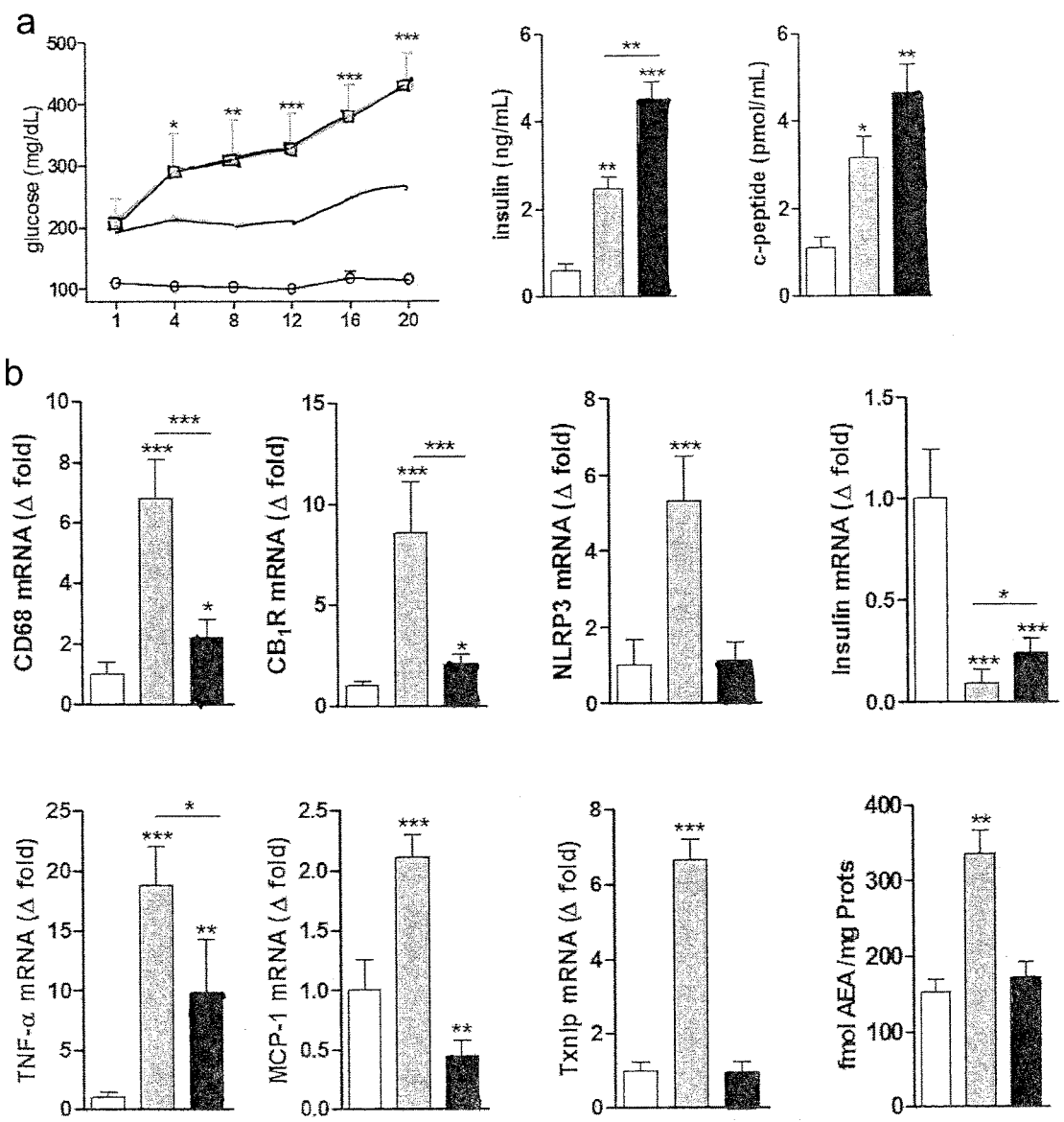
FIG. 8 shows that depletion of macrophages delays the progression of diabetes and prevents inflammatory cell infiltration and pro-inflammatory signaling in pancreatic islets.

Clodronate, a chemical agent that induce macrophage apoptosis, was used to deplete macrophages. Treatment of ZDF rats with clodronate-containing liposomes delayed the onset of hyperglycemia and prevented the progressive decrease in plasma insulin and c-peptide (FIG. 8a). Clodronate treatment also prevented infiltration of islets by macrophages, and attenuated the expression of the macrophage-derived cytokines MCP-1 and TNFα (FIG. 8b). Increases in pancreatic anandamide, $CB_1R$, Nlrp3 and Txnip mRNA and Nlrp3 protein were similarly normalized, compatible with infiltrating macrophages being their main source. Pancreatic insulin content was modestly increased.

Example 4. Selective Knockdown of Macrophage $CB_1R$ Protects ZDF Rats from Diabetes Peritoneal Macrophage Preparation and Gene Silencing by siRNA/EP Particles In Vitro Eight-week old ZDF rats were injected i.p. with 4% thioglycollate broth (Sigma-Aldrich). Five days following injection, the peritoneal cavity was washed with PBS and peritoneal fluid was filtered through a 70 μm diameter pore nylon mesh and centrifuged. The pellet was first treated with red blood cell lysis buffer and plated in DMEM supplemented with 10% fetal bovine serum (FBS), 50 μg/ml streptomycin and 50 units/ml penicillin. 24 hours after isolation peritoneal elicited cells (PEC) were treated with siRNA. Eighty, 160 or 240 pmoles of scrambled or $CB_1R$ siRNA (Dharmacon) was incubated with 3 nmoles EP in PBS for 15 min and added to $1\times10^6$ cells. 48 hours after treatment, mRNA were extracted, reversed transcribed and the degree of $CB_1R$ knock-down was analyzed by qPCR.

Preparation of Glucan Encapsulated siRNA Particles (GeRPs) and In Vivo Administration Fluorescein (FITC)-labeled glucan shells were prepared as previously described (Tesz, et al. 2011 *Biochemical Journal* 436:351-362). To prepare a GeRP dose for one rat, 50 nmoles siRNA (Dharmacon) were incubated with 500 nmoles Endo-Porter (Gene Tools) in 30 mM sodium acetate pH 4.8 for 15 min at RT in a final volume of 200 μl. The siRNA/Endo-Porter solution was added to 10 mg (≈1010) of FITC-glucan shells and then vortexed and incubated for 1 hour. The siRNA loaded GeRPs were then resuspended in 5 ml PBS and sonicated to ensure homogeneity of the GeRP preparation.

Twelve 8-week old ZDF rats were then injected i.p. once a day for ten days with 5.6 mg/kg GeRPs loaded with 2.1 mg/kg EP and 0.436 mg/kg siRNA. 6 rats were then treated with a scrambled (control) siRNA, while 6 other rats received a siRNA directed against rat $CB_1R$ (sense: GCAU-CAAGAGCACCGUUAAUU (SEQ ID NO:9), antisense: UAACGGUGCUCUUGAUGCUU (SEQ ID NO:10)). Thus, the role of macrophage $CB_1R$ in the hyperglycemia and associated proinflammatory changes was tested in ZDF rats given daily i.p. injections of siRNA delivery vehicles (GeRPs) composed of β-1,3-D-glucan-encapsulated $CB_1R$ siRNA for 10 days to induce macrophage-specific knockdown of $CB_1R$ (Nature 458, 1180-1184 (2009); Biochem J 436, 351-362 (2011)). Controls received GeRPs containing the scrambled siRNA. In preliminary experiments, the siRNA selected for in vivo use produced dose-dependent, >95% suppression of $CB_1R$ mRNA and no change in $CB_2R$ mRNA in thioglycollate-induced, peritoneal elicited macrophages (PEC) (FIG. 9a). The selective uptake of GeRPs was tested in peripheral blood leukocytes or PECs collected at the end of treatment and immunostained for CD68 and CD3 proteins for FACS analysis.

Cell Preparation and Fluorescence Flow Cytometry Analysis of CD3+ and CD68+ Cells from Blood and Peritoneal Cavity Fluorescence flow cytometry analyses were performed to determine uptake of GeRP by macrophages versus lymphocytes and to estimate the proportion of CD68+ and CD3+ cells in a white blood cell fraction and in peritoneal exudate of GeRPs-treated ZDF rats. PEC were prepared as previously and the white blood cell fraction was prepared by adding 250 μL of whole blood into a red blood cell lysis buffer for 5 min and centrifuged at 500×g for 10 min. The resulting pellets were washed in PBS containing 2% fetal bovine serum and cells were then preincubated with Rat BD Fc BLOCK™ (purified mouse anti-rat CD32, BD Biosciences 550270, San Diego, Calif.) at 4° C. for 10 minutes and then stained for CD3 (Mouse anti-Rat CD3: ALEXA FLUOR™ 647, AbD serotec MCA772A647) or CD68 (Mouse anti-Rat CD68: ALEXA FLUOR™ 647, AbD serotec MCA341A647) for 30 minutes at 4° C. Flow cytometry analysis was performed using a FACS Calibur (BD Biosciences) and quantification of CD3+ and CD68+ cells was achieved using Flowjo software.

As documented previously (Aouadi, M., et al. Orally delivered siRNA targeting macrophage Map4k4 suppresses systemic inflammation. Nature 458, 1180-1184 (2009)), no GeRPs were detectable in peripheral blood monocytes (FIG. 9b), whereas GeRPs were enriched approximately 10-fold in $CD68^+$ PECs over $CD3^+$ lymphocytes (FIG. 9c). ZDF rats treated with $CB_1R$ siRNA remained normoglycemic and hyperinsulinemic, whereas those receiving scrambled siRNA developed progressive hyperglycemia and a decline in plasma insulin and c-peptide similar to that in vehicle-treated ZDF rats (FIG. 10a). $CB_1R$ siRNA treatment also increased insulin expression and content in islets, and decreased macrophage infiltration and the expression of Nlrp3-ASC, IL-1β, IL-18, as well as MCP-1 and $CB_1R$ (FIG. 10b). These effects were similar to those seen after JD5037 or clodronate treatment.

Example 5. Anandamide Induces Proinflammatory Signaling in Cultured Macrophages

To further define the cells responsible for $CB_1R$-mediated proinflammatory signaling, anandamide was tested in cultured RAW264.7 macrophages and MIN6 insulinoma cells.

Inflammasome Characterization

Active form of p65 NFkB was determined using the TransAM® NFκB Transcription Factor ELISA Kit (Active Motif), Caspase-1 activity was determined using the Caspase 1 assay Kit (Fluorometric) from Abcam (ab39412), IL-1β was measured using the IL-1β Rat ELISA Kit (abcam), and IL-18 with the IL-18 Rat ELISA Kit (Life Technologies).

Cell Culture and Extraction

Mouse RAW264.7 macrophages (ATCC, Manassas, Va.) were cultured as previously described (Liu, et al. 2003 *J Biol Chem* 278:45034-45039) and were either treated during 4 hours with various concentrations of AEA (0.1, 0.5, 1, and 10 μM) and/or JD5037 (100 nM) or treated with 30 ng/mL of IL-1β (Abcam Ab9723). Mouse MIN6 insulinoma cells were a gift from NIDDK and were cultured in low glucose All extractions were followed by DNase I treatment (Invitrogen). Total mRNA was reverse-transcribed using the ISCRIPT™ cDNA kit (Bio-Rad). Real-time PCR was performed as described previously (Jourdan, et al. 2010 *Diabetes* 59:926-934) in a 96-well plate using a STEPONE-PLUS™ real time PCR system (Applied Biosystems). QUANTITECT™ Primer Assays were used to detect gene expression (Table 3, which lists the primers used for rat and mice (tissue)). Expression of the gene of interest is reported as a relative value comparing it to the geometric average of 18S, L19, L38 and TATA box binding protein expression.

TABLE 3

| Rats primers | | | | Mouse Primers | |
|---|---|---|---|---|---|
| Gene | Reference | Gene | Reference | Gene | Reference |
| 18S | QT00199374 | IFN-g | QT00184982 | L19 | QT01779218 |
| AdipoR1 | QT01811922 | IL-10 | QT00177618 | TBP | QT00198443 |
| AdipoR2 | QT01595580 | IL-12 | QT00188839 | 18S | QT01036875 |
| AIM-2 | QT02376171 | IL-18 | QT00183071 | Nlrp3 | QT00122458 |
| Arginase 1 | QT00177611 | IL-1b | QT00181657 | Caspase 1 | QT00199458 |
| ASC | QT00368676 | IL-1R | QT00178920 | CB1 | QT01748831 |
| BAK | QT02346736 | IL-1Ra | QT00193970 | CB2 | QT00159558 |
| BAX | QT01081752 | Il-4 | QT01590316 | insulin | QT01660855 |
| Bcl-2 | QT00184863 | insulin | QT00373303 | BAK | QT00246988 |
| Bcl-xl | QT01081346 | L19 | QT01810704 | BAX | QT00102536 |
| CB1 | QT00191737 | L38 | QT01612625 | Bcl-2 | QT02392292 |
| CB2 | QT0013004 | MCP-1 | QT00183253 | Bcl-xl | QT00149254 |
| CD3 | QT01587803 | Nlrp3 | | | |
| CD4 | QT00181811 | Nlrp6 | QT01080401 | | |
| CD68 | QT00372204 | Nlrp12 | QT01591744 | | |
| FAS | QT00196595 | NOS | QT00178325 | | |
| Fas | QT00196595 | SCD-1 | QT02285493 | | |
| FasL | QT00178171 | TBET | QT01690143 | | |
| Fat-CD36 | QT01830395 | TBP | QT01605632 | | |
| Foxp3 | QT00451633 | TGF-b | QT00187796 | | |
| Gata3 | QT00192885 | TNF-a | QT00178717 | | |
| glucokinase | QT00182966 | TNF-R1 | QT01599738 | | |
| Glut 2 | QT00192822 | Txnip | QT00368984 | | |
| iFi16 | QT00463393 | | | | |

DMEM (Gibco 11885) supplemented with 15% FBS (BenchMark 100-006) and 1% antibiotic antimycotic cocktail (Invitrogen 15240-096). Cells were either treated during 4 hours with various concentrations of AEA (0.5, 1 and 5 μM) or treated with 30 ng/mL of IL-1β (Abcam Ab9723).

For both cell types, medium was collected and immediately frozen in liquid nitrogen. Cells were washed twice in ice-cold sterile PBS before harvesting. EC (endocannabinoid) levels were determined as previously 3, secretion of IL-1β, IL-18, TNF-α and MCP-1 in the medium were determined using ELISA kits (Biosensis BEK-2151-2P, Uscn Life Science & Technology Company E90064Mu, Biosensis BEK-2102-2P, Uscn Life Science & Technology Company E90087Mu, respectively).

Western-Blotting

MIN6 cells were treated either with vehicle, IL-1β (30 ng/mL), IL1R antagonist (10 ng/mL) for 3 hours or pretreated 1 h with IL1R antagonist (10 ng/mL) followed by 3 h incubation with IL-1β (30 ng/mL). $CB_1R$ relative protein content was assessed by Western blotting using a CB1 Receptor Polyclonal Antibody (Cayman, 101500) and revealed using an Anti-beta Actin antibody coupled to HRP (Abcam, ab49900). Blot quantification was performed using the gel analysis options of image J software.

Real-time PCR

Total mRNA from the liver, pancreas and kidney were extracted with Trizol (Invitrogen), while total mRNA from cells was extracted using RNEASY™ Mini Kit (Qiagen).

Statistics

Values are expressed as mean±SEM. Data were subjected to one-way analysis of variance, followed by the Tukey-Kramer post-hoc test. Time-dependent variables were analyzed and results in multiple groups were compared by ANOVA followed by Bonferroni test. (GraphPad Prism version 6 for Windows). Significance was at $P<0.05$.

In RAW264.7 cells, anandamide markedly increased the secretion of IL-1β, TNF-α, and MCP-1, with peak changes observed at 0.5 μM, whereas it did not affect the much lower levels of these cytokines detectable in the medium of MIN6 cells (FIG. 11a). Similarly, anandamide robustly increased the expression of Nlrp3 and caspase-1 in macrophages but not in β-cells, and caused a much greater increase in $CB_1R$ expression in the former, without affecting $CB_2R$ expression (FIG. 11a).

The above findings suggest that endocannabinoids induce β-cell apoptosis indirectly through macrophage-derived cytokines. However, they could also act directly on $CB_1R$ present on β-cells. Therefore, the effects of anandamide and IL-1β on the gene expression of pro- and anti-apoptotic proteins and insulin in MIN6 cells were compared (FIG. 11b). Both compounds were used at maximally effective concentrations for reducing insulin gene expression (0.5 μM anandamide or 30 ng/mL IL-1β). Anandamide had little or no effect on pro- and anti-apoptotic gene expression, whereas IL-1β markedly induced the pro-apoptotic genes Bak and Bax, and drastically suppressed the anti-apoptotic genes Bcl-2 and Bcl-xl (FIG. 11b). IL-1β also drastically reduced CB₁R mRNA and protein, which was blocked by the IL-1R antagonist (FIG. 11c).

Example 6. siRNA Targeting Analysis of Human CNR1 Gene

Computerized analysis of the human CNR1 gene was undertaken to identify ideal regions within the human CNR1 gene against which siRNA can be directed. Sequence regions were selected based on the following criteria: excluding regions with a) GC content of <30% or >64%; b) motifs correlated with toxicity; c) containing known miRNA seed region motifs, d) containing known SNPs. This analysis identified the regions of SEQ ID NO:13 listed in Table 4.

TABLE 4 siRNA targets within the human CNR1 gene

| Sequence | SEQ ID NO | CNR1 Transcript Region |
|---|---|---|
| TG GGTCACTTTC TCAGTCATTT TGAGCTCAGC CTAA | 14 | T259-A294 |
| TCCG CACCATCACC ACTGACCTC | 15 | T347-C369 |
| AGTCCC TTCCAAGAGA AGATGACTGC GGGAGACAAC CCCCAGCTAG TCCCAG | 16 | A475-G526 |
| GTGGGGAGA ACTTCATGGA CATAGAGTGT TTCATGGTCC TGAACCCCAG CCAGCAGCT | 17 | G602-T659 |
| GTGCGTCA TCCTCCACTC CCGCAGCCTC CGCTGCAGGC | 18 | G723-C798 |

TABLE 4-continued siRNA targets within the human CNR1 gene

| Sequence | SEQ ID NO | CNR1 Transcript Region |
|---|---|---|
| CTTCCTACCA CTTCATCGGC AGCCTGGCGG TGGCAGAC TGTTCC ACCGCAAAGA TAGC | 19 | T845-C864 |
| TG TTCCTCACAG CCATCGACAG GTACATATCC ATTCACAGGC CCCTGGCCTA TAAGAGGA | 20 | T929-A988 |
| GG CTGGAACTGC GAGAAACT | 21 | G1069-T1088 |
| GATGAAAC CTACCTGATG TTCTGGATCG GGGTCACCAG CGTACTGCTT CTGTTCATCG TG | 22 | G1123-G1182 | siRNAs with overlapping sequences that cover the CNR1 regions listed in Table 4 were tested and the results demonstrated that siRNAs directed to these regions produce greater than 70% knockdown of CB1 receptor mRNA levels in the human macrophage cell line THP1.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention.

What is claimed is:

1. A siRNA compound with strands consisting of between 15 and 40 nucleotides, comprising a nucleotide sequence at least 90% complementary to a contiguous portion of SEQ ID NO:13, corresponding to a cDNA sequence selected from the group consisting of SEQ ID NOs:14-18 and 20-22, as measured over the entire length of the compound, encapsulated in a glucan.

2. The compound according to claim 1, wherein the compound is 100% complementary to a contiguous portion of SEQ ID NO:13, corresponding to a cDNA sequence selected from the group consisting of SEQ ID NOs:14-18 and 20-22 as measured over the entire length of the compound.

3. The compound according to claim 1, wherein the compound comprises at least one nucleotide selected from the group consisting of xanthine, diaminopurine, 8-oxo-$N_6$-methyladenine, 7-deazaxanthine, 7-deazaguanine, $N_4,N_4$-ethanocytosin, $N_6,N_6$-ethano-2,6-diaminopurine, 5-methylcytosine, 5-($C_3$-$C_6$)-alkynylcytosine, 5-fluorouracil, 5-bromouracil, pseudoisocytosine, 2-hydroxy-5-methyl-4-triazolopyridin, isocytosine, isoguanin, and inosine.

4. The compound according to claim 1, wherein the compound is complexed with α-helical amphipathic peptide Endoporter (EP).

5. The compound according to claim 1, wherein the compound is siRNA complexed with a-helical amphipathic peptide Endoporter (EP) and encapsulated in a glucan.

6. The compound according to claim 1, wherein the glucan is β-1,3-D-glucan.

7. A pharmaceutical composition comprising the compound of claim 1 and an ingredient selected from the group consisting of a pharmaceutically acceptable carrier, a diluent, a penetration enhancer, an excipient, and combinations thereof.

8. The pharmaceutical composition of claim 7, wherein the compound is a pharmaceutically acceptable salt.

9. A method of treating or preventing type 2 diabetes mellitus in a subject, comprising administering an effective amount of a composition comprising the glucan-encapsulated siRNA compound of claim 1 directed against cannabinoid receptor 1 (CNR1), to a subject in need thereof, wherein the glucan encapsulation results in uptake of the siRNA by phagocytic macrophages upon administration to the subject.

10. The method of claim 1, wherein the CB1 receptors in the macrophages are knocked down by at least about 70%.

11. The method of claim 1, wherein the glucan is β-1,3-D-glucan.

12. The method of claim 1, wherein the siRNA is complexed with α-helical amphipathic peptide EP prior to glucan encapsulation.

13. The method of claim 1, wherein the subject is suffering from type 2 diabetes mellitus.

14. The method of claim 13, wherein the subject displays at least one of resistance to insulin, and non-functioning beta cells.

15. The method of claim 1, wherein the glucan-encapsulated siRNA directed against a region of cannabinoid receptor 1 (CNR1), wherein the siRNA comprises a sense strand and an antisense strand, wherein the antisense strand is a RNA sequence consisting of a CNR1 cDNA sequence selected from the group consisting of SEQ ID NOs:14-18 and 20-22.

* * * * *

UNITED STATES PATENT AND TRADEMARK OFFICE
CERTIFICATE OF CORRECTION

PATENT NO. : 10,077,446 B2
APPLICATION NO. : 14/900951
DATED : September 18, 2018
INVENTOR(S) : George Kunos et al.

It is certified that error appears in the above-identified patent and that said Letters Patent is hereby corrected as shown below:

In the Claims

In Column 64, Claim 10, Lines 30-31, please delete "The method of claim 1, wherein the CB1 receptors in the macrophages are knocked down by at least 70%." and insert --The method of claim 9, wherein the CNR1 receptors in the macrophages are knocked down by at least 70%.--

In Column 64, Claim 11, Line 32, please delete "The method of claim 1,..." and insert --The method of claim 9,...--

In Column 64, Claim 12, Line 34, please delete "The method of claim 1,..." and insert --The method of claim 9,...--

In Column 64, Claim 13, Line 37, please delete "The method of claim 1,..." and insert --The method of claim 9,...--

In Column 64, Claim 15, Line 42, please delete "The method of claim 1,..." and insert --The method of claim 9,...--

Signed and Sealed this
Sixth Day of November, 2018

Andrei Iancu
*Director of the United States Patent and Trademark Office*

SEQUENCE LISTING

```
<160> NUMBER OF SEQ ID NOS: 22

<210> SEQ ID NO 1
<211> LENGTH: 5465
<212> TYPE: DNA
<213> ORGANISM: Rattus norvegicus

<400> SEQUENCE: 1
ttaggtcgtt aggagaactt actgtgaaca ggctctttta tttcttcaaa agatgtctcc      60
catttcaagc aaggagcacc catggctgag ggttccctcc cggcatctct ttctcagtca     120
ccttgagtct ggcctaatca aagactgagg ttatgaagtc gatcctagat ggccttgcag     180
acaccacctt ccgtaccatc accacagacc tcctctacgt gggctcgaat gacattcagt     240
atgaagatat caaaggagac atggcatcca aattaggata cttcccacag aaattccctc     300
taacttcctt caggggtagt cccttccaag aaaagatgac cgcaggagac aactcccgt      360 tggtcccagc aggagacaca acaaacatta cagagttcta taacaagtct ctctcgtcgt     420
tcaaggagaa tgaggagaac atccagtgtg gggagaactt tatggacatg gagtgcttta     480
tgattctgaa tcccagccag cagctggcca tcgctgtact gtccctcaca ctgggcacct     540
tcacggttct ggagaaccta ctggtgctgt gtgtcatcct gcactcccgc agtctccgat     600
gcaggccttc ctaccacttc atcggcagcc tggcagtggc cgacctcctg ggaagtgtca     660
tttttgtgta cagctttgtt gacttccatg tattccaccg taaagacagc cccaatgtgt     720
```

```
ttctgttcaa actgggtggg gttacagcct ccttcacagc ttctgtgggc agcctgttcc    780
tcacagccat cgacaggtac atatccattc acaggcctct ggcctataag aggatcgtca    840
ccaggcccaa ggccgttgtg gccttttgcc tgatgtggac tatcgcaata gtaatcgctg    900
tgttgcctct cctgggctgg aactgcaaga agctgcaatc tgtttgctcg gacattttcc    960
cactcattga cgagacctac ctgatgttct ggattggggt gaccagtgtg ctgctgctgt   1020
tcattgtgta cgcgtacatg tacattctct ggaaggctca cagccacgcg gtccgcatga   1080
ttcagcgtgg gacccagaag agcatcatca tccacacgtc agaagacggc aaggtgcagg   1140
tgacccggcc tgaccaagcc cgcatggaca ttaggctggc caaaaccctg gttctgatcc   1200
tggtggtgtt gatcatctgc tggggccctc tgcttgcgat catggtgtat gacgtcttcg   1260
ggaagatgaa caagcttatc aagacggtgt ttgccttctg cagtatgctc tgcctgctga   1320
actccaccgt gaacccatc atctatgctc tgaggagcaa ggacctgaga catgctttcc   1380
gaagcatgtt cccttcgtgc gaaggcaccg cacagcctct agacaacagc atgggggact   1440
cagactgcct gcacaagcac gccaacaaca cagccagcat gcacagggcc gcggagagct   1500
gcatcaagag caccgttaag atcgcgaagg tgaccatgtc tgtgtccaca gacacgtccg   1560
ccgaggctct gtgagcctgc tgcttttgtg gctgcacaga aaaagaaaaa aagttttct    1620
ttagcttaaa acttagaagt ctgttgtctc atcggttaca tatatatttt taagtttacc   1680
gtgtttagta aaatagtgac tgtcaccgtg cttactgagt ttgctgacat ctcaatagct   1740
taggtactta aactccattt cccagggtt tacagtgtag aaagcctatt gcttcagtta   1800
ctcggtggtc cttcaaagtc tctgaaatag aagggaaaac tttggcttcc aaatccgaag   1860
cctaactatc catagaaaat caccatgaaa tgagtaataa cctttgtaac cacaactttc   1920
atgatgctgt gtctgtccac agtattaaag aggtacattt ttaccataag tatagtgcta   1980
aagtagagaa actttgtaac ctgttttctg tcccctgtta gttgtgtgtt gtgtcagtgt   2040
ttaatatgtc agtttattta tttatttatt tttgtctagc ttagcaaaac cagaatgtag   2100
ccctcataag agcgatggca tacaagagtg attgtgtagc agggcgaccc ctgtttagat   2160
agtattactg tccatgatac gattttagaa accttagtat ttcttccaat atccgtatct   2220
aaagttaata ttgacataag cataaaggtt tattttcctg ttaaaacaac aagaagaatt   2280
tgaagactgt tcaaagtatt gagcagaatt catggacact taaaactgtg ttaggcctgc   2340
atttcgtag gaggacattt caatatcttc tggaccacag ctgttcagtt gggtaatgga    2400
ttgtgatcag aatggaaaag agaaagtaac actgactttc aaagctgacg ccctgacttt   2460
ctgcagtcgt tagctataac tggacctctt aagacagcat gtgtcaacct tagtgtatac   2520
tgttatcact gtggagttgc tgttcacctg ccgtgtatcg catcgttatg ttctggattt   2580
aaatagattt caggcccgga tggccaaaag acagtttgtc ttctccttaa ttgagaagag   2640
acattgtctg gcttagtaaa attgtgagtg tgattgtaaa tgtgtatgtg tgtgtatgtg   2700
tgtgtatgtg tgtgtgtgca tgtgtgtgta ttctatcttg caactgttac agccatgtcc   2760
ccacaggaga aaaaccgacc aagtgtgaga cgtaccccctt gctgcaccct tgcacatgga   2820
tttagttgct gcaattgagc tctttgtgaa atcctgttta taaaaattct gactgaaact   2880
tctcaggagt cttcccacct aggagattgg gttgagaatt ctcgtgacgt ttaggtgttc   2940
tgtaaggcca gcagcgttca gcaagaagta atcagtaaga ggtgctggaa agtagaggag   3000
tctcccaggg agaggagagt gtgggggatg gtgggcgcct actattaatc aaagtccttg   3060
caaatggaaa tcagtaaagg gggatggttc tacggccttc ttcaaccccca ccccaccccc   3120
```

```
cacagtagca agtttcaatg gtgcacatca gcagtgcaat ctcaggttaa ggagcaccat    3180
gccagttacc agggccaggc catttcatga cagaggatga gtaggacaga ggatatatat    3240
aacaaatggg cagtgaaaac ctggtgacgg cccagtacct ggctctgttt agatgtttgg    3300
gcaaagcaaa aggcagtgcc tctgcctgct ggtaccaaga tgtgccaaaa cataaggacg    3360
agggtggcta gcttcggttc gacatctctg ccatggtgct caaaatttgg gccttttttc    3420
cgataaagag aagtattgct tttaagaagc cactcactcc tgataaattc tatgtagagt    3480
ctctcctcat acaggttctc ccccgtcctg aggactgcat agcatgaagt ggagagctag    3540
tatatgcctg tgatttctag tgtttggggt tcccagtctg atggggcagt gccccttctt    3600
gcaatcaatg tgacctgagg gccaagctag atatatccta gatttttttt ccagctgagt    3660
ctcttgcttt tcttctctgt gcacagagga ggactcaaga tgctggagga ttagtaactc    3720
catagagaag ggtattgata gaataccacc aggggctagg aattgccagc ctcatcctac    3780
atccacctga atatcaatca tgtctctagc taccaggctg taccacctct tctcacagct    3840
acaaagacct ggtaggacat tctaggtata gttattaaaa aaaaaatcca agattcactt    3900
ttagaactgt atttgtgtaa atgccatttt agtgataaga ttttatagtg tattgaactt    3960
tcaagaccta actcatattt aataagctaa gggccaatgg ggctgatagc actaaacttg    4020
gtgcttattg atactctaag gaatatctgt gaaatatcat catgtgtgcg ttaagctacc    4080
ttcatttaaa gggacttaaa attaggtgga tccactttgg cttttcccat atcatttcct    4140
aaccatattg accaaaacct tttccccagt gagtattagt cattagaatt acattcatta    4200
gtatcattca ttaaccagcc ccttaattag attcattaat ttaaatgatt ttaatttaat    4260
cacttataca ctctggcatc agggttatct acttccctct gacgtttgtc cttaacatgc    4320
attcttcggc cattgctcat ctttaagggg ggctaattcc caaactactt aactttgtcc    4380
aaataaagac tgagtcctag actatcagta tcatttaaac aaagaaagca gtctctaaga    4440
gctcctagat ttaccccctat gtattaaata tatgtaaaaa taaatgtgca tctgggcagc    4500
ttagacataa gtctgtgcca gatgtctcca aagctgtctg atacttaact ttcaggctta    4560
gctggtatca aatgccaagg aattttttgct acctaaaccc atctgcagga aataggccca    4620
actaccagat gagaactagg tctctagtta ccattcattt cattaatttc tgccattcca    4680
tatccataaa cagcaccact aacatcatgc acaagattag attcctaata ttcttgactg    4740
tatatttgta tgatattta aaacctccta aatggccatt cacagttgct ttgcactggc    4800
cttctgataa aatgttaaca cacctattgt aatatacaaa aaacattcta tctactgatt    4860
tggactgaat gtatgtacat aggctttaca aaaagtcag acgtcgaagc agtggtttac    4920
agatcagtga ttttcagata gagtttcttt cagttgccgt ggaatctttc aaaagcactc    4980
ttagtgtgaa cttactgaac tctaggggtc ctggtgatca gagtcgccta gagaggaaac    5040
ctttccttgt attaatatga agcaagatac cagactatct tgattctcac ttccagtgtt    5100
tcaagtggaa aacgtatttc cttgttgtct ctgtaaatgg aacatcctta attttcctct    5160
taaagaatat tgtattgtta gatgtttgtt gaactggtag catcattgag actgctgtga    5220
agtctttgtc agtaatctgt ataatatttt gtatacaagt actggtaaga ttgttattaa    5280
gtgtagctcc agtcattaaa ttactatagc aaagtagtac ttctgtaata tttacaatgt    5340
attaagccta cagtatattt tatttcattg atgtaatttt attgttattt attcaagaga    5400
aagcagttca tcatgtctat tgtctaaaat tacctggaat caaataaaag ttctagatta    5460
```

```
tcacg                                                              5465
```

<210> SEQ ID NO 2
<211> LENGTH: 473
<212> TYPE: PRT
<213> ORGANISM: Rattus norvegicus

<400> SEQUENCE: 2

| Met | Lys | Ser | Ile | Leu | Asp | Gly | Leu | Ala | Asp | Thr | Thr | Phe | Arg | Thr | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Thr | Asp | Leu | Leu | Tyr | Val | Gly | Ser | Asn | Asp | Ile | Gln | Tyr | Glu | Asp |
|     |     |     | 20  |     |     |     |     | 25  |     |     |     |     | 30  |     |     |

| Ile | Lys | Gly | Asp | Met | Ala | Ser | Lys | Leu | Gly | Tyr | Phe | Pro | Gln | Lys | Phe |
|     |     |     | 35  |     |     |     |     | 40  |     |     |     |     | 45  |     |     |

| Pro | Leu | Thr | Ser | Phe | Arg | Gly | Ser | Pro | Phe | Gln | Glu | Lys | Met | Thr | Ala |
|     |     | 50  |     |     |     |     | 55  |     |     |     |     | 60  |     |     |     |

| Gly | Asp | Asn | Ser | Pro | Leu | Val | Pro | Ala | Gly | Asp | Thr | Thr | Asn | Ile | Thr |
| 65  |     |     |     |     | 70  |     |     |     |     | 75  |     |     |     |     | 80  |

| Glu | Phe | Tyr | Asn | Lys | Ser | Leu | Ser | Ser | Phe | Lys | Glu | Asn | Glu | Glu | Asn |
|     |     |     |     | 85  |     |     |     |     | 90  |     |     |     |     | 95  |     |

| Ile | Gln | Cys | Gly | Glu | Asn | Phe | Met | Asp | Met | Glu | Cys | Phe | Met | Ile | Leu |
|     |     |     | 100 |     |     |     |     | 105 |     |     |     |     | 110 |     |     |

| Asn | Pro | Ser | Gln | Gln | Leu | Ala | Ile | Ala | Val | Leu | Ser | Leu | Thr | Leu | Gly |
|     |     | 115 |     |     |     |     | 120 |     |     |     |     | 125 |     |     |     |

| Thr | Phe | Thr | Val | Leu | Glu | Asn | Leu | Leu | Val | Leu | Cys | Val | Ile | Leu | His |
|     | 130 |     |     |     |     | 135 |     |     |     |     | 140 |     |     |     |     |

| Ser | Arg | Ser | Leu | Arg | Cys | Arg | Pro | Ser | Tyr | His | Phe | Ile | Gly | Ser | Leu |
| 145 |     |     |     |     | 150 |     |     |     |     | 155 |     |     |     |     | 160 |

| Ala | Val | Ala | Asp | Leu | Leu | Gly | Ser | Val | Ile | Phe | Val | Tyr | Ser | Phe | Val |
|     |     |     | 165 |     |     |     |     | 170 |     |     |     |     | 175 |     |     |

| Asp | Phe | His | Val | Phe | His | Arg | Lys | Asp | Ser | Pro | Asn | Val | Phe | Leu | Phe |
|     |     |     | 180 |     |     |     |     | 185 |     |     |     |     | 190 |     |     |

| Lys | Leu | Gly | Gly | Val | Thr | Ala | Ser | Phe | Thr | Ala | Ser | Val | Gly | Ser | Leu |
|     |     |     | 195 |     |     |     |     | 200 |     |     |     |     | 205 |     |     |

| Phe | Leu | Thr | Ala | Ile | Asp | Arg | Tyr | Ile | Ser | Ile | His | Arg | Pro | Leu | Ala |
|     |     | 210 |     |     |     |     | 215 |     |     |     |     | 220 |     |     |     |

| Tyr | Lys | Arg | Ile | Val | Thr | Arg | Pro | Lys | Ala | Val | Val | Ala | Phe | Cys | Leu |
| 225 |     |     |     |     | 230 |     |     |     |     | 235 |     |     |     |     | 240 |

| Met | Trp | Thr | Ile | Ala | Ile | Val | Ile | Ala | Val | Leu | Pro | Leu | Leu | Gly | Trp |
|     |     |     | 245 |     |     |     |     | 250 |     |     |     |     | 255 |     |     |

| Asn | Cys | Lys | Lys | Leu | Gln | Ser | Val | Cys | Ser | Asp | Ile | Phe | Pro | Leu | Ile |
|     |     |     | 260 |     |     |     |     | 265 |     |     |     |     | 270 |     |     |

| Asp | Glu | Thr | Tyr | Leu | Met | Phe | Trp | Ile | Gly | Val | Thr | Ser | Val | Leu | Leu |
|     |     | 275 |     |     |     |     | 280 |     |     |     |     | 285 |     |     |     |

| Leu | Phe | Ile | Val | Tyr | Ala | Tyr | Met | Tyr | Ile | Leu | Trp | Lys | Ala | His | Ser |
|     | 290 |     |     |     |     | 295 |     |     |     |     | 300 |     |     |     |     |

| His | Ala | Val | Arg | Met | Ile | Gln | Arg | Gly | Thr | Gln | Lys | Ser | Ile | Ile | Ile |
| 305 |     |     |     |     | 310 |     |     |     |     | 315 |     |     |     |     | 320 |

| His | Thr | Ser | Glu | Asp | Gly | Lys | Val | Gln | Val | Thr | Arg | Pro | Asp | Gln | Ala |
|     |     |     | 325 |     |     |     |     | 330 |     |     |     |     | 335 |     |     |

| Arg | Met | Asp | Ile | Arg | Leu | Ala | Lys | Thr | Leu | Val | Leu | Ile | Leu | Val | Val |
|     |     |     | 340 |     |     |     |     | 345 |     |     |     |     | 350 |     |     |

| Leu | Ile | Ile | Cys | Trp | Gly | Pro | Leu | Leu | Ala | Ile | Met | Val | Tyr | Asp | Val |
|     |     |     | 355 |     |     |     |     | 360 |     |     |     |     | 365 |     |     |

```
    Phe Gly Lys Met Asn Lys Leu Ile Lys Thr Val Phe Ala Phe Cys Ser
        370                 375                 380

Met Leu Cys Leu Leu Asn Ser Thr Val Asn Pro Ile Ile Tyr Ala Leu
    385                 390                 395                 400

Arg Ser Lys Asp Leu Arg His Ala Phe Arg Ser Met Phe Pro Ser Cys
                        405                 410                 415

Glu Gly Thr Ala Gln Pro Leu Asp Asn Ser Met Gly Asp Ser Asp Cys
                    420                 425                 430

Leu His Lys His Ala Asn Asn Thr Ala Ser Met His Arg Ala Ala Glu
                435                 440                 445

Ser Cys Ile Lys Ser Thr Val Lys Ile Ala Lys Val Thr Met Ser Val
        450                 455                 460

Ser Thr Asp Thr Ser Ala Glu Ala Leu
    465                 470

<210> SEQ ID NO 3
<211> LENGTH: 5863
<212> TYPE: DNA
<213> ORGANISM: Homo sapiens

<400> SEQUENCE: 3
gcgccggcgc cgcctcccgc acgctactcc ctctgccacc ccttccttct ccacttcttt      60
tccgcctccg cctcttcttg tctcccgcgg cgccagcgcc ttcccttggc ccgggcgggg     120
gcctcggctc cctgcagagc tctccgtagt cagtggggga tatttcgttc tagcggacaa     180
ccagcccctg agctgggcga gaggtgccaa gggagcttct gtcccgagga ccaggggatg     240
cgaaggggca aagagattga agaggggag tcacataatc agcatacgtt tatgaagatt      300 accccccacag ctgtgtggca agtgatcaaa aaggaacagg accagagaag agcaggaaaa    360
ctggtcagaa agcaggcgcc ctaaccctgg attgcccct gtgggtcact ttctcagtca      420
ttttgagctc agcctaatca aagactgagg ttatgaagtc gatcctagat ggccttgcag     480
ataccacctt ccgcaccatc accactgacc tcctgtacgt gggctcaaat gacattcagt     540
acgaagacat caaaggtgac atggcatcca aattaggta cttcccacag aaattccctt      600
taacttcctt taggggaagt cccttccaag agaagatgac tgcgggagac aaccccccagc    660 tagtcccagc agaccaggtg aacattacag aattttacaa caagtctctc tcgtccttca    720
aggagaatga ggagaacatc cagtgtgggg agaacttcat ggacatagag tgtttcatgg    780
tcctgaaccc cagccagcag ctggccattg cagtcctgtc cctcacgctg gcaccttca    840 cggtcctgga gaacctcctg gtgctgtgcg tcatcctcca ctcccgcagc ctccgctgca    900
ggccttccta ccacttcatc ggcagcctgg cggtggcaga cctcctgggg agtgtcattt    960 tgtctacag cttcattgac ttccacgtgt tccaccgcaa agatagccgc aacgtgtttc    1020
tgttcaaact gggtggggtc acggcctcct tcactgcctc cgtgggcagc ctgttcctca    1080
cagccatcga caggtacata tccattcaca ggccctggc ctataagagg attgtcacca    1140
ggcccaaggc cgtggtggcg ttttgcctga tgtggaccat agccattgtg atcgccgtgc    1200
tgcctctcct gggctggaac tgcgagaaac tgcaatctgt ttgctcagac attttcccac    1260
acattgatga aacctacctg atgttctgga tcggggtcac cagcgtactg cttcgtttca    1320
tcgtgtatgc gtacatgtat attctctgga aggctcacag ccacgccgtc cgcatgattc    1380
agcgtggcac ccagaagagc atcatcatcc acacgtctga ggatgggaag gtacaggtga    1440
cccggccaga ccaagcccgc atggacatta ggttagccaa gacccctggtc ctgatcctgg    1500
```

-continued

```
tggtgttgat catctgctgg ggccctctgc ttgcaatcat ggtgtatgat gtctttggga      1560
agatgaacaa gctcattaag acggtgtttg cattctgcag tatgctctgc ctgctgaact      1620
ccaccgtgaa ccccatcatc tatgctctga ggagtaagga cctgcgacac gctttccgga      1680 gcatgttttcc ctcttgtgaa ggcactgcgc agcctctgga taacagcatg ggggactcgg     1740
actgcctgca caaacacgca acaatgcag ccagtgttca cagggccgca gaaagctgca       1800
tcaagagcac ggtcaagatt gccaaggtaa ccatgtctgt gtccacagac acgtctgccg      1860
aggctctgtg agcctgatgc ctccctggca gcacaggaaa agaatttttt tttttaagct      1920
caaaatctag aagagtctat tgtctccttg gttatatttt tttaactttta ccatgctcaa    1980 tgaaaaggtg attgtcacca tgatcactta tcagtttgct aatgtttcca tagtttaggt     2040
actcaaactc cattctccag gggtttacag tgaagaaagc ctgttgttta agtgactgaa     2100
cgatccttca aagtctcaat gaaataggag ggaaaccttt ggctacacaa ttggaagtct    2160
aagaacccat ggaaaaatgc catcaaatga ataatgcctt tgtaaccaca actttcacta    2220
taatgtgaaa tgtaactgtc cgtagtatca gagatgtcca ttttttacaag ttatagtact   2280 agagatattt tgtaaaatgt attatgtcct gtgagatgtg tatcagtgtt tatgtgctat    2340
taatatttgt ttagttcagc aaaactgaaa ggtagacttt tatgagaaca atggacaagc    2400
agtggatacg tgtcaatgtg tgcactttt ttctatatta ttgcccatga tataacttta     2460
gaaataaacc ttaatatttc ttcaaatatc tctatttaat tttgacactg aaataaccgt    2520
aaaggtttat ttttctgtta cctcaacaag aagaatttga agacttcaaa atattgagca    2580
gaattcattc atacttaaaa atttattagc cctgcatttt cataggaaga cacattatct   2640
tctggactat agctgttcta atggattata atcagaatgg aagagagaaa gcatattgac   2700 ttttttttgag cgacatctct gactttcttt agtctttagc tattactgga tctcttaaga   2760
cagcatgtgt taatcttaat gtatatcgtt atcactgtgc agttgctgtt tacttgaata   2820
gtattgtgtt cctatattcc aggtttaagt agatttcatg cctgggtggc caaacaacag    2880
tcttcatttt ttttaattga aaagaagtag tgtctggatc agtaaaatta tactgtgtgt    2940
gagtgtgaat ataaatgtgt gtatgtgtgt ttctgtcctg taactgttac agtaatgtca    3000
taaagtgaga aaactgtgac caagtataaa ctttttaccac ttgctgcact cttgcacatg    3060
gattcagttt ctaaaattga gttcttcctg taatcttgtt gataaaaata ctgactccaa    3120
ccattcaaaa atttcacccc atccctcctt aagagattgg atcaagtatt actaaattga    3180
cctttaggta ttacacaaga ccagtgctta gcaaaaaata atgacaggca tccaaggaag    3240 ggatgtatt gtagtgttat tgccaggaaa ggagagtact ttggtttctg agcaccgaat    3300
attgagcaat atgtcagtca ctaaaaggaa gacagttcta cagaaaaaca atggtaacat   3360
ttttcaatag cgtgtgtaga tagtatgcac tatatacatc acgttaaagt aggactatca    3420
cacccagccc atgtggctaa aaaagctgaa tcagacagtg gatgagacac acaacggcag    3480
tgaagaaccg atacacttgg cattgacgtc tagctatgct gtatctgtgc tttgcccaca    3540
tgcccttggt gacagctgag cacccagctc tgtcttggta ggtttgggct aaggaacaaa    3600
tctctccttt gctcgtggtt agcaagatac actcaagcat gaagataaac acagctgctt    3660
tcttcttaca ccccggtctc atgctcctta atggcgccat gggtgcttgt tgggccttttt   3720 tccagtaagg aatgatattg ctgaagaatc tacttaaccc tgacaaattt taattataat   3780
ctcttcttat acagataaaa catgactcct acaaggcccc aaggtttaca tagtctgaag    3840
tgaagtacag agctggcatc tatctggtga tttctagctc tcgagatacc caagcagcct    3900
```

```
gatgggcag ttccccttct tacggttcac gctctaaggc aggatgtggc ttatgagata    3960
ctttgcattg tctgtctgca caccttgaat ctgcctgctg gctcccttac tttacctctc   4020
tgtcatgtgc agatgaaggc tcagggtgct agaggattag taagatctct ttctaaagac   4080
aggagagatt atttacaaga gaactcacc agggtttagt ttgcatttaa gaattgccag    4140
tcttttgtcc tgcatcatct tgaacattaa tccacatgtt tcagagctca ccaggcagta   4200
ccaatgctct tttcacagct atgaagagct agagaaattc ttgttatggt agaaaaattt   4260
cacgattcat ttttgaaact gcatttgtgc gtatgcagtg tagattttat agtgtgttgt   4320
gctttcaaga tctaaatcat atataataaa ttaagggaca atggggctga cagcactaaa   4380
cttggtgctt attgatattc taagaaatat ctgtgaaata tcatcacgta tgttatacaa   4440
ccttcattta aaaaggttta aaactagtta gattcacttt gacactttc atatcatttc    4500
ttaacccaag tgacgaaaac attgtcccca atgaatatac tcattagaat taccatttgt   4560
taatatcact cattaattaa ccccataatt agatccatta atttaaatga tttaaattta   4620
agtaagtttt ataaggtctg acatcagagg tatcttactt tcctctgagg atgatgtact   4680
tgccctgacc atgcatttta ccatcacaca tgttcagaaa gggccaaatt cccaacctgc   4740
tcatttttt tttatcagag tcatgatgaa tcagtcctag aatgtttcat ttgcacaagt    4800
agggctgcct ccaagaggaa cctctgattt attttgtatg aaatatatgt gaaaggatat   4860
gaatctgaga gatgctgtag acatctgtcc tacacttgag atgatttcca agcctctctg   4920
gcactttgag ttaagtctat ctggtattaa atgccaagga ccttttgctg cctaaatcca   4980
ctctgcagga ataggccca accaccagat gagaattagg ccctggatga gtagcgctat    5040
agttactgtc ctgttgatta atttctgcca tttcatgtcc ataaaagaga ccacccatat   5100
catgcacaca attagatttc tcacactcta actgtatatt tgtatgatat tttaaaatct   5160
cctaaatgct gggcaatggc tattaacaat taattgtctt gcactggcct tctgatgaaa   5220
tgttaacaat gcctattgta atatagaaaa aaacattcta tctactgatt tgggctgaat   5280
gtatgtaaat aggtttctaa aaagtcagat gtttgagcag tggcctacaa atcagtaatt   5340
ttcggatggg agagtttctt tacattgccg tggcatctta aaagctatct tcatgtaaat   5400
tgactgtact aggcctactg gggatcagag ttcccaagaa aggaaacctt ttcttgtatc   5460
tggattcaaa tttatttcca atgtttcaag cgggaaacat gactctttat tgtctgtaaa   5520
tctaacatta ttacttttcc tcttagaaga atattgtatt gttagatgtt tgttgagctg   5580
gtaacatcgt tgcaaccact gcaatatctt cgttagtaat ctgtataata ctttgtatac   5640
aagtactggt aagattgtta ttaaatgtag cttcagtcat taaattacta tagcaaagta   5700
gtacttcttc tgtaatattt acaatgtatt aagcccacag tatattttat ttcaatgtaa   5760
ttaaactgtt aacttattca aagagaaaac atctcatcat gtctattgtc caaagttacc   5820
tggaatcaaa taaaaattct agattaccat gaagaacata aaa                     5863
```

<210> SEQ ID NO 4
<211> LENGTH: 472
<212> TYPE: PRT
<213> ORGANISM: Homo sapiens

<400> SEQUENCE: 4

Met Lys Ser Ile Leu Asp Gly Leu Ala Asp Thr Thr Phe Arg Thr Ile
1               5                   10                  15

Thr Thr Asp Leu Leu Tyr Val Gly Ser Asn Asp Ile Gln Tyr Glu Asp

```
                     20                  25                  30
Ile Lys Gly Asp Met Ala Ser Lys Leu Gly Tyr Phe Pro Gln Lys Phe
                35                  40                  45
Pro Leu Thr Ser Phe Arg Gly Ser Pro Phe Gln Glu Lys Met Thr Ala
    50                  55                  60
Gly Asp Asn Pro Gln Leu Val Pro Ala Asp Gln Val Asn Ile Thr Glu
65                  70                  75                  80
Phe Tyr Asn Lys Ser Leu Ser Ser Phe Lys Glu Asn Glu Glu Asn Ile
                85                  90                  95
Gln Cys Gly Glu Asn Phe Met Asp Ile Glu Cys Phe Met Val Leu Asn
                100                 105                 110
Pro Ser Gln Gln Leu Ala Ile Ala Val Leu Ser Leu Thr Leu Gly Thr
            115                 120                 125
Phe Thr Val Leu Glu Asn Leu Leu Val Leu Cys Val Ile Leu His Ser
        130                 135                 140
Arg Ser Leu Arg Cys Arg Pro Ser Tyr His Phe Ile Gly Ser Leu Ala
145                 150                 155                 160
Val Ala Asp Leu Leu Gly Ser Val Ile Phe Val Tyr Ser Phe Ile Asp
                165                 170                 175
Phe His Val Phe His Arg Lys Asp Ser Arg Asn Val Phe Leu Phe Lys
                180                 185                 190
Leu Gly Gly Val Thr Ala Ser Phe Thr Ala Ser Val Gly Ser Leu Phe
            195                 200                 205
Leu Thr Ala Ile Asp Arg Tyr Ile Ser Ile His Arg Pro Leu Ala Tyr
        210                 215                 220
Lys Arg Ile Val Thr Arg Pro Lys Ala Val Val Ala Phe Cys Leu Met
225                 230                 235                 240
Trp Thr Ile Ala Ile Val Ile Ala Val Leu Pro Leu Leu Gly Trp Asn
                245                 250                 255
Cys Glu Lys Leu Gln Ser Val Cys Ser Asp Ile Phe Pro His Ile Asp
                260                 265                 270
Glu Thr Tyr Leu Met Phe Trp Ile Gly Val Thr Ser Val Leu Leu Leu
            275                 280                 285
Phe Ile Val Tyr Ala Tyr Met Tyr Ile Leu Trp Lys Ala His Ser His
        290                 295                 300
Ala Val Arg Met Ile Gln Arg Gly Thr Gln Lys Ser Ile Ile His Thr
305                 310                 315                 320
Thr Ser Glu Asp Gly Lys Val Gln Val Thr Arg Pro Asp Gln Ala Arg
                325                 330                 335
Met Asp Ile Arg Leu Ala Lys Thr Leu Val Leu Ile Leu Val Val Leu
                340                 345                 350
Ile Ile Cys Trp Gly Pro Leu Leu Ala Ile Met Val Tyr Asp Val Phe
            355                 360                 365
Gly Lys Met Asn Lys Leu Ile Lys Thr Val Phe Ala Phe Cys Ser Met
        370                 375                 380
Leu Cys Leu Leu Asn Ser Thr Val Asn Pro Ile Ile Tyr Ala Leu Arg
385                 390                 395                 400
Ser Lys Asp Leu Arg His Ala Phe Arg Ser Met Phe Pro Ser Cys Glu
                405                 410                 415
Gly Thr Ala Gln Pro Leu Asp Asn Ser Met Gly Asp Ser Asp Cys Leu
                420                 425                 430
His Lys His Ala Asn Asn Ala Ala Ser Val His Arg Ala Ala Glu Ser
            435                 440                 445
```

```
Cys Ile Lys Ser Thr Val Lys Ile Ala Lys Val Thr Met Ser Val Ser
    450                 455                 460

Thr Asp Thr Ser Ala Glu Ala Leu
465                 470

<210> SEQ ID NO 5
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 5
gauguggacu aucgcaauau u                                              21

<210> SEQ ID NO 6
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 6
uauugcgaua guccacaucu u                                              21

<210> SEQ ID NO 7
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 7
gccuauaaga ggaucgucau u                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 8
ugacgauccu cuuauaggcu u                                              21

<210> SEQ ID NO 9
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 9
gcaucaagag caccguuaau u                                              21

<210> SEQ ID NO 10
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 10
uuaacggugc ucuugaugcu u                                              21
```

<210> SEQ ID NO 11
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 11
ccguuaagau cgcgaagguu u                                            21

<210> SEQ ID NO 12
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 12
accuucgcga ucuuaacggu u                                            21

<210> SEQ ID NO 13
<211> LENGTH: 1500
<212> TYPE: DNA
<213> ORGANISM: Homo sapiens

<400> SEQUENCE: 13
gcgccggcgc cgcctcccgc acgctactcc ctctgccacc ccttccttct ccacttcttt      60
tccgcctccg cctcttcttg tctcccgcgg cgccagcgcc ttcccttggc ccgggcgggg     120
gcctcggctc cctgcagagc tctccgtagt cagtggggga tatttcgttc tagcggacaa     180
ccagcccctg agctgggcga gaggtgccaa gggagcttct gtcccgagga ccaggggatg     240
cgaagggatt gccccctgtg ggtcactttc tcagtcattt tgagctcagc ctaatcaaag     300
actgaggtta tgaagtcgat cctagatggc cttgcagata ccaccttccg caccatcacc     360
actgacctcc tgtacgtggg ctcaaatgac attcagtacg aagacatcaa aggtgacatg     420
gcatccaaat tagggtactt cccacagaaa ttccctttaa cttcctttag gggaagtccc     480
ttccaagaga agatgactgc gggagacaac ccccagctag tcccagcaga ccaggtgaac     540
attacagaat tttacaacaa gtctctctcg tccttcaagg agaatgagga gaacatccag     600
tgtggggaga acttcatgga catagagtgt ttcatggtcc tgaacccccag ccagcagctg     660 gccattgcag tcctgtccct cacgctgggc accttcacgg tcctggagaa cctcctggtg     720
ctgtgcgtca tcctccactc ccgcagcctc gctgcaggc cttcctacca cttcatcggc     780
agcctggcgg tggcagacct cctggggagt gtcattttg tctacagctt cattgacttc     840
cacgtgttcc accgcaaaga tagccgcaac gtgtttctgt tcaaactggg tggggtcacg     900
gcctccttca ctgcctccgt gggcagcctg ttcctcacag ccatcgacag gtacatatcc     960
attcacaggc ccctggccta taagaggatt gtcaccaggc caaggccgt ggtggcgttt    1020 tgcctgatgt ggaccatagc cattgtgatc gccgtgctgc ctctcctggg ctggaactgc    1080
gagaaactgc aatctgtttg ctcagacatt ttcccacaca ttgatgaaac ctacctgatg    1140
ttctggatcg gggtcaccag cgtactgctt ctgttcatcg tgtatgcgta catgtatatt    1200
ctctggaagg ctcacagcca cgccgtccgc atgattcagc gtggcaccca aagagcatc    1260 atcatccaca cgtctgagga tgggaaggta caggtgaccc ggccagacca agcccgcatg    1320
gacattaggt tagccaagac cctggtcctg atcctggtgg tgttgatcat ctgctgggc    1380 cctctgcttg caatcatggt gtatgatgtc tttgggaaga tgaacaagct cattaagacg    1440

```
gtgtttgcat tctgcagtat gctctgcctg ctgaactcca ccgtgaaccc catcatctat       1500
```

<210> SEQ ID NO 14
<211> LENGTH: 36
<212> TYPE: DNA
<213> ORGANISM: Homo sapiens

<400> SEQUENCE: 14

```
tgggtcactt tctcagtcat tttgagctca gcctaa                                  36
```

<210> SEQ ID NO 15
<211> LENGTH: 23
<212> TYPE: DNA
<213> ORGANISM: Homo sapiens

<400> SEQUENCE: 15

```
tccgcaccat caccactgac ctc                                                23
```

<210> SEQ ID NO 16
<211> LENGTH: 52
<212> TYPE: DNA
<213> ORGANISM: Homo sapiens

<400> SEQUENCE: 16

```
agtcccttcc aagagaagat gactgcggga gacaaccccc agctagtccc ag                52
```

<210> SEQ ID NO 17
<211> LENGTH: 58
<212> TYPE: DNA
<213> ORGANISM: Homo sapiens

<400> SEQUENCE: 17

```
gtggggagaa cttcatggac atagagtgtt tcatggtcct gaaccccagc cagcagct          58
```

<210> SEQ ID NO 18
<211> LENGTH: 76
<212> TYPE: DNA
<213> ORGANISM: Homo sapiens

<400> SEQUENCE: 18

```
gtgcgtcatc ctccactccc gcagcctccg ctgcaggcct tcctaccact tcatcggcag        60
cctggcggtg gcagac                                                        76
```

<210> SEQ ID NO 19
<211> LENGTH: 20
<212> TYPE: DNA
<213> ORGANISM: Homo sapiens

<400> SEQUENCE: 19

```
tgttccaccg caaagatagc                                                    20
```

<210> SEQ ID NO 20
<211> LENGTH: 60
<212> TYPE: DNA
<213> ORGANISM: Homo sapiens

<400> SEQUENCE: 20

```
tgttcctcac agccatcgac aggtacatat ccattcacag gccccctggcc tataagagga       60
```

<210> SEQ ID NO 21
<211> LENGTH: 20
<212> TYPE: DNA

```
<213> ORGANISM: Homo sapiens

<400> SEQUENCE: 21
ggctggaact gcgagaaact                                               20

<210> SEQ ID NO 22
<211> LENGTH: 60
<212> TYPE: DNA
<213> ORGANISM: Homo sapiens

<400> SEQUENCE: 22
gatgaaacct acctgatgtt ctggatcggg gtcaccagcg tactgcttct gttcatcgtg   60
```